United States Patent
Golan et al.

(10) Patent No.: US 11,694,807 B2
(45) Date of Patent: Jul. 4, 2023

(54) METHOD AND SYSTEM FOR COMPUTER-AIDED DECISION GUIDANCE

(71) Applicant: Viz.ai Inc., San Francisco, CA (US)

(72) Inventors: David Golan, San Francisco, CA (US); Christopher Mansi, San Francisco, CA (US)

(73) Assignee: Viz.ai Inc., San Francisco, CA (US)

( * ) Notice: Subject to any disclaimer, the term of this patent is extended or adjusted under 35 U.S.C. 154(b) by 0 days.

(21) Appl. No.: 17/843,099

(22) Filed: Jun. 17, 2022

(65) Prior Publication Data

US 2022/0406460 A1 Dec. 22, 2022

Related U.S. Application Data

(60) Provisional application No. 63/212,005, filed on Jun. 17, 2021.

(51) Int. Cl.
*G16H 50/20* (2018.01)
*G16H 30/40* (2018.01)
*G16H 30/20* (2018.01)
*G16H 40/20* (2018.01)

(52) U.S. Cl.
CPC .............. *G16H 50/20* (2018.01); *G16H 30/40* (2018.01); *G16H 30/20* (2018.01); *G16H 40/20* (2018.01)

(58) Field of Classification Search
CPC ........ G16H 50/20; G16H 30/40; G16H 40/20; G16H 30/20
USPC ........................................................ 705/2–3
See application file for complete search history.

(56) References Cited

U.S. PATENT DOCUMENTS

| | | |
|---|---|---|
| 6,349,330 B1 | 2/2002 | Bernadett et al. |
| 8,374,414 B2 | 2/2013 | Tang et al. |
| 9,307,918 B2 | 4/2016 | Kinrot et al. |
| 9,439,622 B2 | 9/2016 | Case et al. |
| 10,346,979 B2 | 7/2019 | Mansi et al. |
| 10,373,315 B2 | 8/2019 | Mansi et al. |
| 10,835,257 B2 | 11/2020 | Ferrera et al. |
| 10,853,449 B1 | 12/2020 | Nguyen et al. |
| 2004/0161137 A1 | 8/2004 | Aben et al. |
| 2006/0140473 A1 | 6/2006 | Brooksby et al. |

(Continued)

FOREIGN PATENT DOCUMENTS

| | | |
|---|---|---|
| JP | 2004243117 A | 9/2004 |
| JP | 1854717 B2 | 11/2011 |

(Continued)

OTHER PUBLICATIONS

Cai, Zhaowei, et al., "Cascade R-CNN: High Quality Object Detection and Instance Segmentation", https://arxiv.org/pdf/1906.09756.pdf, Jun. 24, 2019.

(Continued)

*Primary Examiner* — Michael Tomaszewski
(74) *Attorney, Agent, or Firm* — Jeffrey Schox; Caitlin Ploch

(57) ABSTRACT

A system for computer-aided decision guidance includes and/or interfaces with a computing system. A method for computer-aided decision guidance includes: receiving a set of data; determining a set of parameters associated with the set of data; and triggering an output based on the set of parameters. Additionally or alternatively, the method can include analyzing the set of data and/or any other suitable processes.

20 Claims, 12 Drawing Sheets

(56) References Cited

U.S. PATENT DOCUMENTS

| | | | |
|---|---|---|---|
| 2007/0019846 A1 | 1/2007 | Bullitt et al. | |
| 2008/0021502 A1 | 1/2008 | Imielinska et al. | |
| 2009/0028403 A1 | 1/2009 | Bar-Aviv et al. | |
| 2009/0129649 A1 | 5/2009 | Djeridane | |
| 2009/0279752 A1 | 11/2009 | Sirohey et al. | |
| 2010/0106002 A1 | 4/2010 | Sugiyama et al. | |
| 2011/0028825 A1* | 2/2011 | Douglas | G06T 19/00 600/407 |
| 2011/0052024 A1 | 3/2011 | Nowinski | |
| 2011/0116702 A1 | 5/2011 | Bredno et al. | |
| 2011/0172550 A1 | 7/2011 | Martin et al. | |
| 2012/0065987 A1 | 3/2012 | Farooq et al. | |
| 2012/0237103 A1 | 9/2012 | Hu | |
| 2013/0185096 A1 | 7/2013 | Giusti et al. | |
| 2013/0208955 A1 | 8/2013 | Zhao et al. | |
| 2013/0208966 A1 | 8/2013 | Zhao et al. | |
| 2014/0142982 A1 | 5/2014 | Janssens | |
| 2014/0142983 A1 | 5/2014 | Backhaus et al. | |
| 2014/0222444 A1 | 8/2014 | Cerello et al. | |
| 2014/0257854 A1 | 9/2014 | Becker et al. | |
| 2014/0348408 A1 | 11/2014 | Zhu et al. | |
| 2015/0011902 A1 | 1/2015 | Wang | |
| 2015/0104102 A1 | 4/2015 | Carreira et al. | |
| 2015/0208994 A1 | 7/2015 | Rapoport | |
| 2015/0320365 A1 | 11/2015 | Schulze et al. | |
| 2016/0037057 A1 | 2/2016 | Westin et al. | |
| 2016/0063191 A1 | 3/2016 | Vesto et al. | |
| 2016/0100302 A1 | 4/2016 | Barash et al. | |
| 2016/0110890 A1 | 4/2016 | Smith | |
| 2016/0135706 A1 | 5/2016 | Sullivan et al. | |
| 2016/0180042 A1 | 6/2016 | Menon et al. | |
| 2016/0188829 A1 | 6/2016 | Southerland et al. | |
| 2017/0007167 A1 | 1/2017 | Kostic et al. | |
| 2017/0143428 A1 | 5/2017 | Raffy et al. | |
| 2017/0147765 A1 | 5/2017 | Mehta | |
| 2017/0228501 A1 | 8/2017 | Turner et al. | |
| 2017/0228516 A1 | 8/2017 | Sampath et al. | |
| 2017/0258433 A1 | 9/2017 | Gulsun et al. | |
| 2017/0300654 A1 | 10/2017 | Stein et al. | |
| 2017/0340260 A1 | 11/2017 | Chowdhury et al. | |
| 2018/0025255 A1 | 1/2018 | Poole et al. | |
| 2018/0046759 A1* | 2/2018 | Barral | G06T 7/0014 |
| 2018/0085001 A1 | 3/2018 | Berger et al. | |
| 2018/0110475 A1 | 4/2018 | Shaya | |
| 2018/0116620 A1 | 5/2018 | Chen et al. | |
| 2018/0235482 A1 | 8/2018 | Fonte et al. | |
| 2018/0253530 A1 | 9/2018 | Goldberg et al. | |
| 2018/0365824 A1 | 12/2018 | Yuh et al. | |
| 2018/0365828 A1 | 12/2018 | Mansi et al. | |
| 2018/0366225 A1 | 12/2018 | Mansi et al. | |
| 2019/0198160 A1* | 6/2019 | Barral | G06V 10/25 |
| 2019/0380643 A1 | 12/2019 | Kochura et al. | |
| 2020/0058410 A1 | 2/2020 | Khouri et al. | |
| 2020/0294241 A1 | 9/2020 | Wu et al. | |
| 2020/0364587 A1* | 11/2020 | Kapur | G16H 30/40 |
| 2021/0137384 A1 | 5/2021 | Robinson et al. | |
| 2021/0334958 A1 | 10/2021 | Siow et al. | |
| 2022/0130547 A1* | 4/2022 | Grady | G06V 30/19147 |
| 2022/0180518 A1* | 6/2022 | Agus | G16H 50/20 |

FOREIGN PATENT DOCUMENTS

| | | |
|---|---|---|
| JP | 2012027565 A | 2/2012 |
| WO | 2016134125 A1 | 8/2016 |

OTHER PUBLICATIONS

He, Kaiming, et al., "Mask R-CNN", https://arxiv.org/pdf/1703.06870.pdf, Jan. 24, 2018.

Ker, Justin, et al., "Image Thresholding Improves 3-Dimensional Convolutional Neural Network 1-21 Diagnosis of Different Acute Brain Hemorrhages on Computed Tomography Scans", Sensors 2019, 2167, May 10, 2019, www.mdpi.com.com/journal/sensors.

Keshavamurthy, K., et al., "Machine learning algorithm for automatic detection of CT-identifiable hyperdense lesions associated with traumatic brain injury", Mar. 23, 2017, SPIE Medical Imaging, Orlando, Florida.

Kirisil, H.A., et al., "Standardized evaluation framework for evaluating coronary artery stenosis detection, stenosis quantification and lumen segmentation algorithms in computed tomography angiography", Elsevier, 2013, pp. 859-876.

Lewis, Thomas L., et al., "Ambulance smartphone tool for field triage of ruptured aortic aneurysms (FILTR): study protocol for a prospective observational validation of diagnostic accuracy", BMJ Open 2016, pp. 1-5, https://bmjopen.bmj.com/content/bmjopen/6/10/e011308.full.pdf.

Lidayova, Kristina, et al., "Skeleton-based 1-3,6-15 fast, fully automated generation of vessel tree structure for clinical evaluation of blood vessel systems", In: Skeletonization : theory, methods and applications, Jun. 1, 2017.

Liu, Liyuan, et al., "On the Variance of the Adaptive Learning Rate and Beyond", https://arxiv.org/pdf/1908.03265.pdf, Apr. 17, 2020, Published as a conference paper at ICLR 2020.

Madhuripan, Nikhil, et al., "Computed Tomography Angiography in Head and Neck Emergencies", Seminars in Ultrasound and CT and MRI, US, vol. 38, No. 4, 2017. Feb. 20, 2017 (Feb. 20, 2017), pp. 345-356.

Smith, Wade S., et al., "Prognostic Significance of Angiographically Confirmed Large Vessel Intracranial Occlusion in Patients Presenting With Acute Brain Ischemia", Neurocritical Care, vol. 4, 2006.

Yu, Y., et al., "Use of Deep Learning to Predict Final Ischemic Stroke Lesions From Initial Magnetic Resonance maging", Mar. 1, 2020, https://europepmc.org/article/med/32163165.

\* cited by examiner

Radius measurements associated with segmented vessel region immediately adjacent to (e.g., proximal to, before, etc) occlusion Parameter 1: diameter at occlusion Parameter 2: aorta to occlusion length under US 11,694,807 B2

METHOD AND SYSTEM FOR COMPUTER-AIDED DECISION GUIDANCE

CROSS-REFERENCE TO RELATED APPLICATIONS

This application claims the benefit of U.S. Provisional Application No. 63/212,005, filed 17 Jun. 2021, which is incorporated in its entirety by this reference.

TECHNICAL FIELD

This invention relates generally to the signals processing and decision-making fields, and more specifically to a new and useful system and method for computer-aided care decision guidance in the signals processing and decision-making fields.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
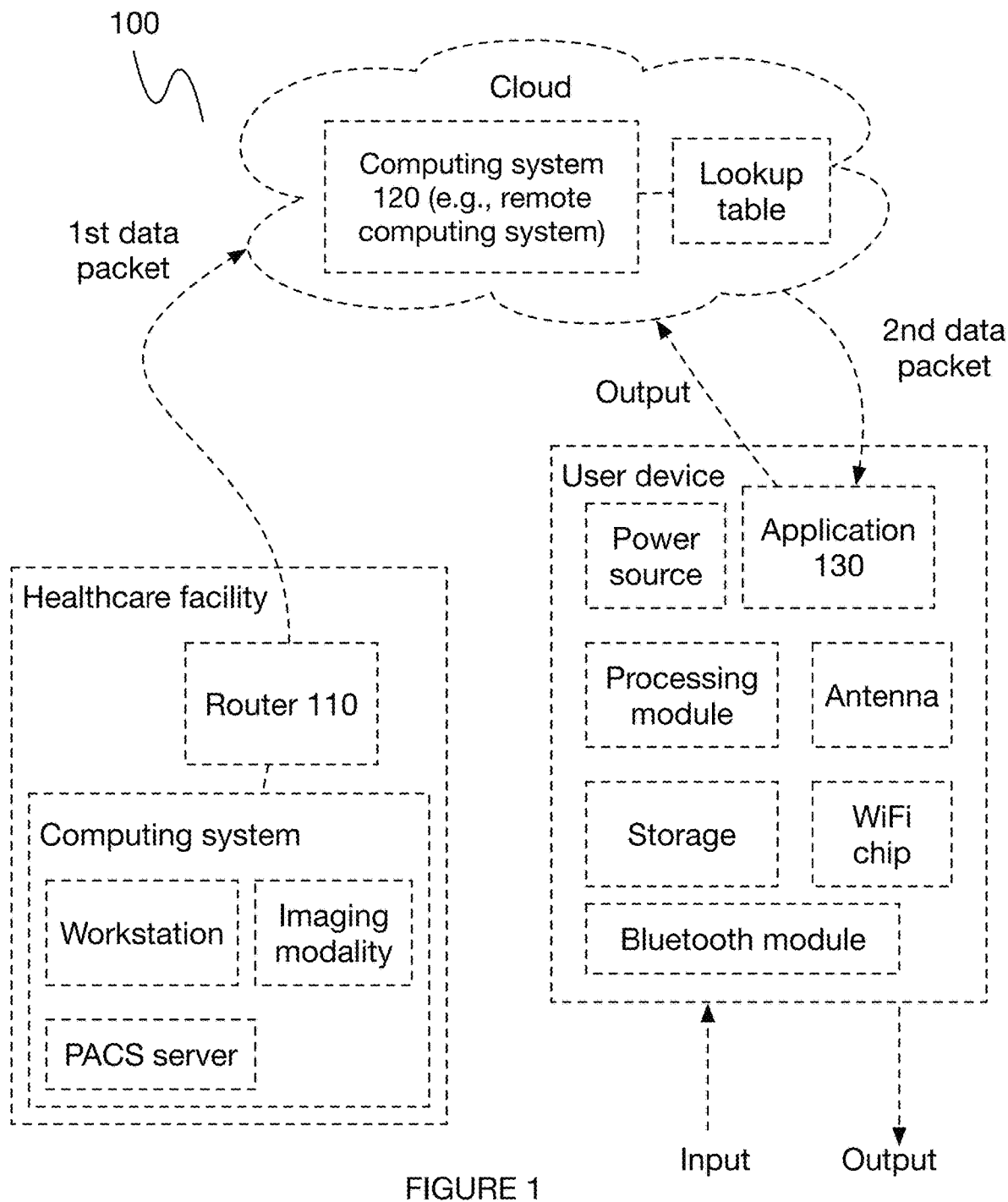
FIG. 1 is a schematic of a system for computer-aided decision guidance.

As shown in FIG. 1, a system 100 for computer-aided decision guidance includes and/or interfaces with a computing system. Additionally or alternatively, the system can include and/or interface with an application and/or any other components.

Further additionally or alternatively, the system 100 can include and/or interface with any or all of the systems, components, embodiments, and/or examples described in any or all of: U.S. application Ser. No. 16/012,458, filed 19 Jun. 2018, U.S. application Ser. No. 16/012,495, filed 19 Jun. 2018, U.S. application Ser. No. 16/913,754, filed 26 Jun. 2020, U.S. application Ser. No. 16/938,598, filed 24 Jul. 2020, U.S. application Ser. No. 17/001,218, filed 24 Aug. 2020, and U.S. application Ser. No. 16/688,721, filed 19 Nov. 2019, and U.S. application Ser. No. 17/385,326, filed 26 Jul. 2021, each of which is incorporated in its entirety by this reference.

Figure 2:
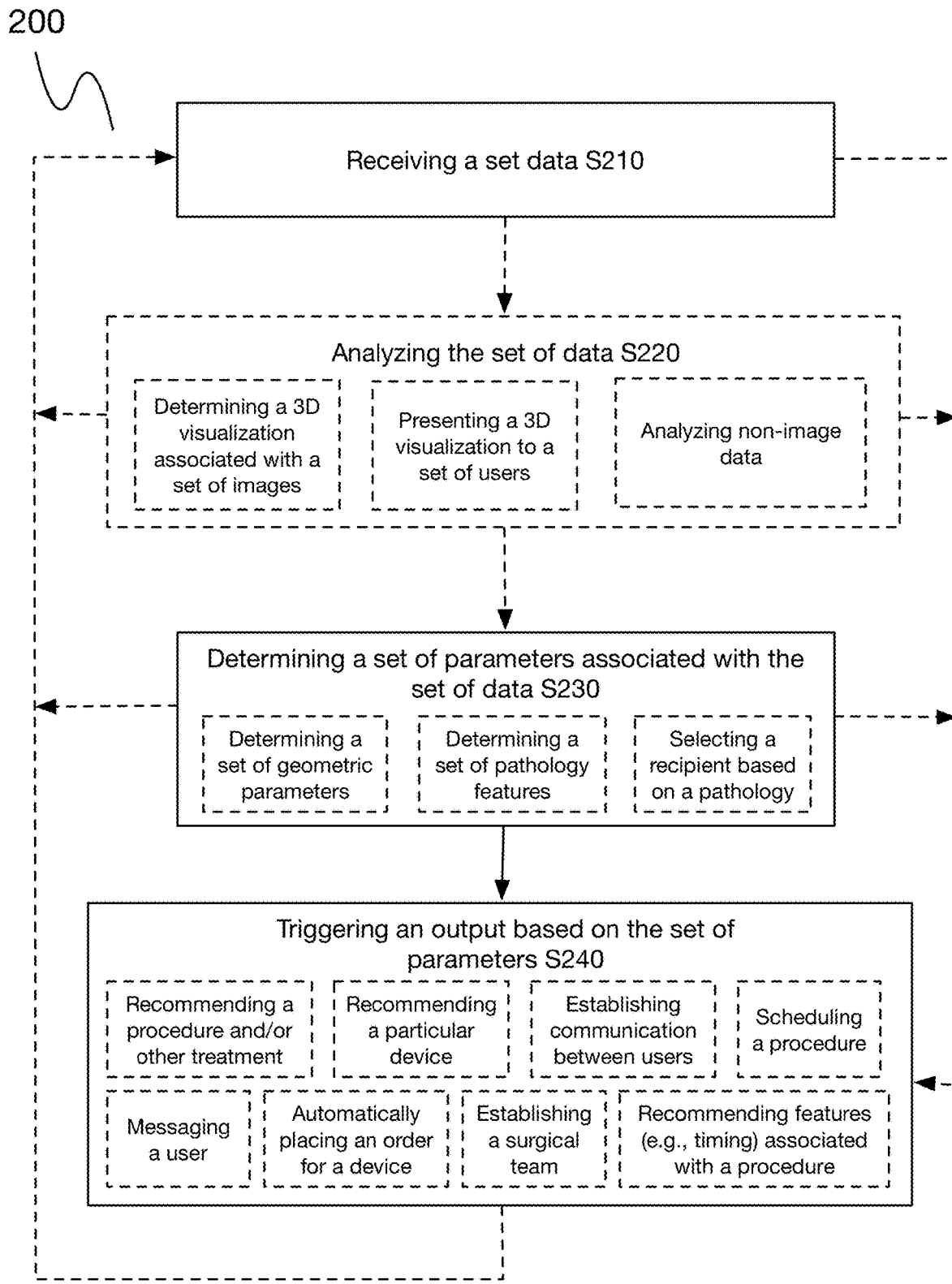
FIG. 2 is a schematic of a method for computer-aided decision guidance.

As shown in FIG. 2, a method 200 for computer-aided decision guidance includes: receiving a set of data S210; determining a set of parameters associated with the set of data S230; and triggering an output based on the set of parameters S231. Additionally or alternatively, the method 200 can include analyzing the set of data S220 and/or any other suitable processes performed in any suitable order.

Further additionally or alternatively, the method can include any or all of the methods, processes, embodiments, and/or examples as described in U.S. application Ser. No. 16/012,458, filed 19 Jun. 2018, U.S. application Ser. No. 16/012,495, filed 19 Jun. 2018, U.S. application Ser. No. 16/913,754, filed 26 Jun. 2020, U.S. application Ser. No. 16/938,598, filed 24 Jul. 2020, U.S. application Ser. No. 17/001,218, filed 24 Aug. 2020, and U.S. application Ser. No. 16/688,721, filed 19 Nov. 2019, and U.S. application Ser. No. 17/385,326, filed 26 Jul. 2021, each of which is incorporated in its entirety by this reference, or any other suitable processes performed in any suitable order. The method 200 can be performed with a system as described above and/or any other suitable system.

The method 200 can be performed with a system as described above and/or any other suitable system.

2. Benefits

The system and method for computer-aided decision guidance can confer several benefits over current systems and methods.

In a first variation, the technology confers the benefit of helping physicians make fast and accurate decisions related to the treatment (e.g., surgery, drug administration, etc.) of patients experiencing an acute, time-sensitive condition (e.g., stroke), which can in turn function to reduce waste, improve outcomes, and/or otherwise benefit the patient or users. In specific examples, this is enabled through any or all of: warning surgeons of obstacles that may cause delays during a procedure (e.g., recommending a point of entry for a catheter, highlighting vascular geometries and properties which may be difficult or impossible to navigate with certain catheters, etc.); preventing surgeons from having to try multiple devices to successfully perform the surgery; reducing the waste associated with incorrect device choice; reducing the number of secondary procedures needed to correct for a non-optimal first procedure; and/or perform any other functions.

In a second variation, additional or alternative to the first, the technology confers the benefit of providing a mobile platform with which to prep and/or plan for surgeries or other treatments. In specific examples, this can enable any or all of: viewing images and/or models of images at a client application (e.g., while the surgeon is en route to the healthcare facility and/or to the patient), prepping for a surgery earlier than conventionally enabled (e.g., selecting medical devices to be ready for surgery before reaching the healthcare facility, selecting medical devices to be ready for surgery before or in parallel with viewing images at a workstation, etc.), establishing communication between multiple care team members and/or between a care team member and a medical technician prepping for the surgery, scheduling a surgery earlier than conventionally scheduled, and/or can perform any other functions. In a particular specific example, for instance, the system and method enable 3D modeling of the images to be viewed at a client application executable on mobile devices of the users (e.g., surgeons, care team members, etc.), such that the users can view the 3D models and plan for surgeries in a mobile and/or remote setting relative to the healthcare facility. Additionally or alternatively, the system and method can enable viewing and/or interactions at an augmented reality (AR) system, a virtual reality (VR) system, a mixed reality (MR), other extended reality (XR) systems, and/or any other systems.

In a third variation, additional or alternative to those described above, the technology confers the benefit of automatically producing one or more outputs related to the treatment of a patient presenting with an acute condition, such as any or all of: making an automatic recommendation of a device for surgery (e.g., automatically selecting a catheter type or size based on a set of machine learning models); automatically triggering the selection of a device for surgery (e.g., automatically messaging a surgical technologist to prepare a device for surgery); automatically triggering a call with a medical device sales representative; automatically messaging a medical device sales representative to confirm a device recommendation; automatically scheduling a surgery; automatically assembling a care team for surgery; and/or performing any other actions.

Additionally or alternatively, can be performed in non-acute settings (e.g., to plan for surgeries in the future).

Additionally or alternatively, the system and method can confer any other benefit.

3. System

As shown in FIG. 1, a system 100 for computer-aided decision guidance includes and/or interfaces with a computing system. Additionally or alternatively, the system can include and/or interface with an application and/or any other components.

Further additionally or alternatively, the system 100 can include and/or interface with any or all of the systems, components, embodiments, and/or examples described in any or all of: U.S. application Ser. No. 16/012,458, filed 19 Jun. 2018, U.S. application Ser. No. 16/012,495, filed 19 Jun. 2018, U.S. application Ser. No. 16/913,754, filed 26 Jun. 2020, U.S. application Ser. No. 16/938,598, filed 24 Jul. 2020, U.S. application Ser. No. 17/001,218, filed 24 Aug. 2020, and U.S. application Ser. No. 16/688,721, filed 19 Nov. 2019, and U.S. application Ser. No. 17/385,326, filed 26 Jul. 2021, each of which is incorporated in its entirety by this reference.

The system 100 functions to provide a platform with which to quickly determine and optionally execute on an optimal treatment plan for a patient (e.g., presenting with an acute condition). Additionally or alternatively, the system 100 can function to: efficiently transmit information to one or more users, alert users to important and/or critical information (e.g., while preventing notification fatigue), establish communication between users, enabling the sharing (e.g., confidential sharing, HIPAA-compliant sharing, de-identified sharing, etc.) of information between users, form and/or initiate a care team for the patient, assign the patient to one or more users and/or care teams, trigger one or more other actions (e.g., selection of a medical device, assignment of patient to a clinical trial, transfer of patient to another point of care, etc.), manage and check in on follow-up for the patient, and/or can perform any other functions.

Additionally or alternatively, the system 100 can function to process a set of images (e.g., with AI, with machine learning, with deep learning, etc.) in order to determine one or more suspected conditions and/or can perform any other suitable functions.

The system 100 is preferably used to perform any or all of the method 200 described below, but can additionally or alternatively be used to perform any other suitable methods.

The system preferably interfaces with one or more points of care (e.g., $1^{st}$ point of care, $2^{nd}$ point of care, $3^{rd}$ point of care, etc.). A point of care preferably refers to a healthcare facility (e.g., a hospital, clinic, urgent care center, rehabilitation center, etc.), but can additionally or alternatively refer to a particular physician involved in the treatment of the patient, a particular procedure assigned to the patient, a particular device and/or treatment (e.g., medication) to be administered to the patient, and/or any other location, person, and/or item involved in the care of the patient.

In a set of variations, for instance, a $1^{st}$ point of care refers to the healthcare facility at which a patient presents, typically where the patient first presents (e.g., in an emergency setting). Conventionally, healthcare facilities include spoke facilities, which are often general (e.g., non-specialist, emergency, etc.) facilities, as well as hub (e.g., specialist) facilities, which can be equipped or better equipped (e.g., in comparison to spoke facilities) for certain procedures (e.g., mechanical thrombectomy), conditions (e.g., stroke), or patients (e.g., high risk). Patients typically present at a spoke facility as the $1^{st}$ point of care, but can alternatively present to a hub facility, such as when it is evident what condition their symptoms reflect, when they have a prior history of a serious condition, when the condition has progressed to a high severity, when a hub facility is closest, randomly, or for any other reason. A healthcare facility can include any or all of: a hospital, clinic, ambulance, doctor's office, imaging center, laboratory, primary stroke center (PSC), comprehensive stroke center (CSC), stroke ready center, interventional ready center, rehabilitation facility, or any other suitable facility involved in patient care and/or diagnostic testing.

A patient can be presenting with symptoms of a condition, no symptoms (e.g., presenting for routine testing), or any combination. In use cases in which a patient is presenting with a condition, the condition can be any or all of: an emergency condition (e.g., urgent condition), a non-emergency (e.g., non-urgent) condition (e.g., chronic pain), and/or any other suitable conditions. The condition can be associated with any suitable body part and/or class of condition, such as, but not limited to, any or all of: brain conditions (e.g., stroke, aneurysm, brain cancer, brain tumor, brain bleeding, traumatic brain injury, cerebral edema, etc.), cardiac conditions (e.g., heart attack, arrhythmia, etc.), pulmonary conditions (e.g., lung disease, pulmonary embolism, asthma attack, etc.), muscular conditions, bone conditions (e.g., bone cancer, bone breaks and/or fractures, etc.), cancers, tumors, blockages, mental health conditions (e.g., depression, suicidal ideation, bipolar disorder, etc.), and/or any other conditions.

A user herein refers to anyone using the system and/or interfacing with the method, such as someone having an account at a client application (e.g., as described above), someone in contact with someone having an account (e.g., who can be reached by someone having an account), and/or any suitable individual involved in the care and/or consult of a patient. A user can optionally be a healthcare worker, wherein a healthcare worker refers to any individual or entity associated with a healthcare facility, such as, but not limited to: a physician, emergency room physician (e.g., orders appropriate lab and imaging tests in accordance with a stroke protocol), radiologist (e.g., on-duty radiologist, healthcare worker reviewing a completed imaging study, healthcare working authoring a final report, etc.), neuroradiologist, specialist (e.g., neurovascular specialist, vascular neurologist, neuro-interventional specialist, neuro-endovascular specialist, expert/specialist in a procedure such as mechanical thrombectomy, cardiac specialist, pulmonary specialist, oncologist, surgeon, etc.), administrative assistant, healthcare facility employee (e.g., staff employee), emergency responder (e.g., emergency medical technician), or any other suitable individual. A user can additionally or alternatively be any or all of: an individual associated with a clinical trial (e.g., clinical trial coordinator, clinical trial recruiter, principal investigator, administrator, etc.), a medical device representative (e.g., who advises on which medical device is suitable for a procedure), and/or any other user.

Any or all of the system can optionally be configured for any or all of: a specific user (e.g., his or her notification preferences, his or her preferred patient lists, etc.), a group and/or team associated with the user (e.g., a cardiac team's preferences at a particular healthcare facility), a healthcare facility (e.g., scheduling information for on-call vs. off-call physicians), and/or any other entities. Additionally or alternatively, any or all of the system can be uniform among users and/or otherwise configured.

3.1 System—Router 110

Figure 4:
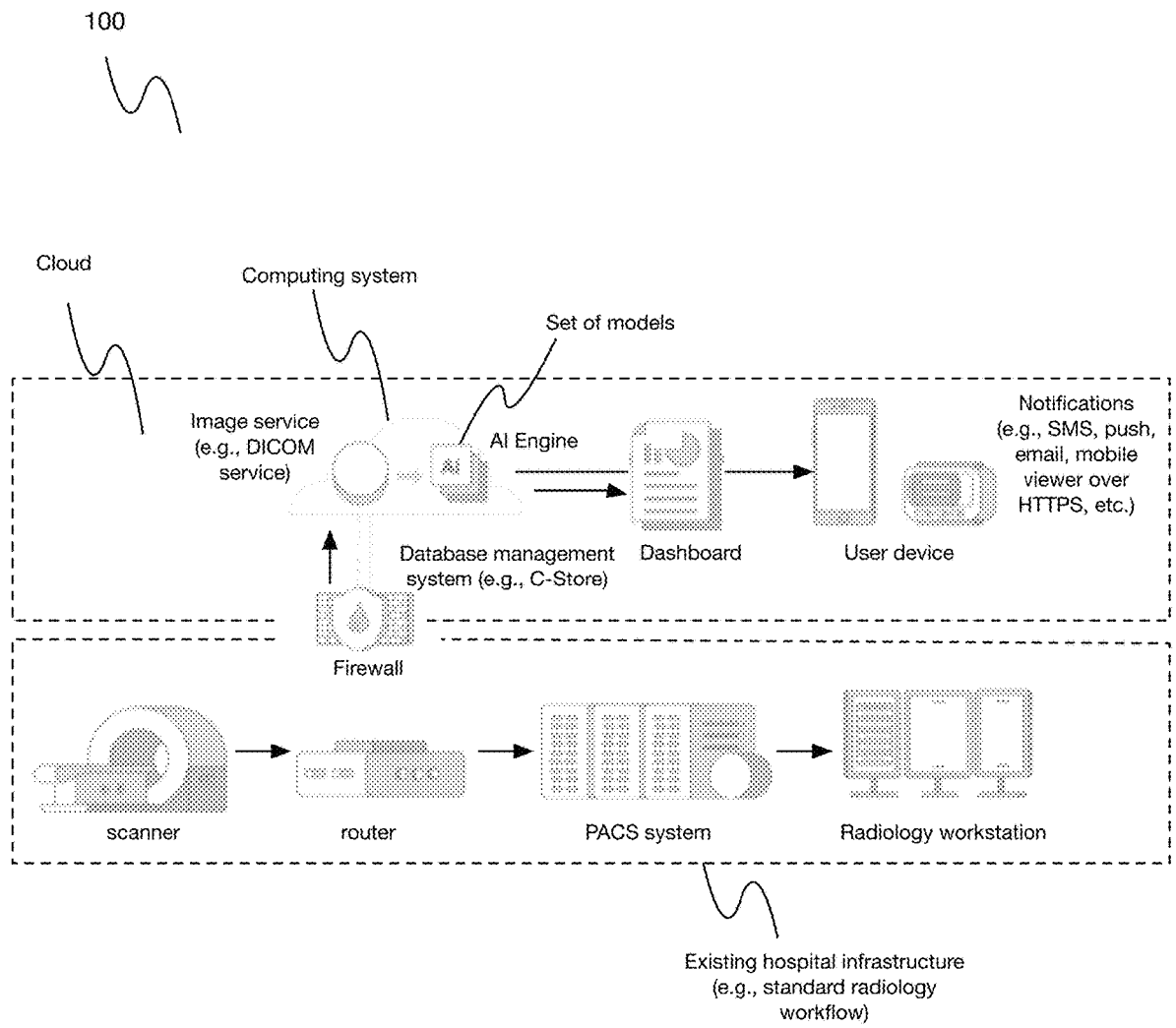
FIG. 4 depicts a schematic variation of the system and method for computer-aided decision guidance.

The system 100 can optionally include and/or interface with a router 110 (e.g., medical routing system, DICOM router, as shown in FIG. 4, etc.), which functions to receive data (e.g., a dataset) to process (e.g., during the method 200). The data can optionally include images (equivalently referred to herein as instances and scans) taken at an imaging modality (e.g., scanner) and optionally via a computing system (e.g., scanner, workstation, PACS server) associated with a point of care. The images can be in the Digital Imaging and Communications in Medicine (DICOM) file format (e.g., generated and transferred between computing system in accordance with a DICOM protocol), and/or in any suitable format. The images preferably include (e.g., are tagged with) and/or are associated with a set of metadata, but can additionally or alternatively include multiple sets of metadata, no metadata, extracted (e.g., removed) metadata (e.g., for regulatory purposes, HIPAA compliance, etc.), altered (e.g., encrypted, decrypted, deidentified, anonymized etc.) metadata, or any other suitable metadata, tags, identifiers, or other suitable information. In some variations, the method 200 includes removing any or all of the metadata prior to providing the instances at a mobile device.

Additionally or alternatively, the data can include any suitable medical data (e.g., diagnostic data, patient data, patient history, patient demographic information, etc.), such as, but not limited to, PACS data, Health-Level 7 (HL7) data, electronic health record (EHR) data, or any other suitable data, and to forward the data to a remote computing system. Further additionally, or alternatively, the data can include non-image data, such as any other diagnostic information. In some variations, for instance, the data includes electrical signals, such as electrocardiogram (ECG) data, which can be processed. Further additionally or alternatively, the data can include any other signals and/or other data in any suitable data formats.

The router 110 can include a virtual entity (e.g., virtual machine, virtual server, etc.), a physical entity (e.g., local server), or any combination. The router can be local (e.g., at a $1^{st}$ healthcare facility, $2^{nd}$ healthcare facility, etc.) and associated with (e.g., connected to) any or all of: on-site server associated with any or all of the imaging modality, the healthcare facility's PACS architecture (e.g., server associated with physician workstations), any suitable medical records databases (e.g., electronic health records [EHR] database, electronic medical records [EMR] database, etc.), and/or any other suitable local server or DICOM compatible device(s). Additionally or alternatively, the router can be remote (e.g., locate at a remote facility, remote server, cloud computing system, etc.), and associated with any or all of: a remote server associated with the PACS system, a modality, or another DICOM compatible device such as a DICOM router.

The router 110 preferably operates on (e.g., is integrated into) a system (e.g., computing system, workstation, server, PACS server, imaging modality, scanner, etc.) at a $1^{st}$ point of care but additionally or alternatively, at a $2^{nd}$ point of care, remote server (e.g., physical, virtual, etc.) associated with one or both of the $1^{st}$ point of care and the $2^{nd}$ point of care (e.g., PACS server, EHR server, HL7 server), a data storage system (e.g., patient records), or any other suitable system. In some variations, the system that the router operates on is physical (e.g., physical workstation, imaging modality, scanner, etc.) but can additionally or alternatively include virtual components (e.g., virtual server, virtual database, cloud computing system, etc.).

The router 110 is preferably configured to receive data (e.g., instances, images, study, series, etc.) from a data collection device (e.g., an ECG device, signals recording device, an imaging modality [e.g., computed tomography scanner, magnetic resonance imaging scanner, ultrasound machine, etc.], etc.) at a point of care (e.g., spoke, hub, etc.) but can additionally or alternatively receive data from a second point of care (e.g., hub, spoke, etc.), multiple points of care, any other healthcare facility, a location other than a healthcare facility (e.g., ambulance, patient's home, etc.). The router can be coupled in any suitable way (e.g., wired connection, wireless connection, etc.) to the data collection device (e.g., directly connected, indirectly connected via a PACS server, etc.). Additionally or alternatively, the router can be connected to the healthcare facility's PACS architecture and/or other server or database. The router 110 can additionally or alternatively receive any other inputs (e.g., as described below), such as inputs from client applications executing on mobile user devices. Alternatively, any or all of these set of inputs can be otherwise ultimately received (e.g., directly) at a computing system.

In some variations, the router includes a virtual machine operating on a computing system (e.g., computer, workstation, user device, etc.), imaging modality (e.g., scanner), server (e.g., PACS server, server at $1^{st}$ healthcare facility, server at $2^{nd}$ healthcare facility, etc.), or other system. In a specific example, the router is part of a virtual machine server. In another specific example, the router is part of a local server.

3.2 System—Computing System 120

Figure 3:
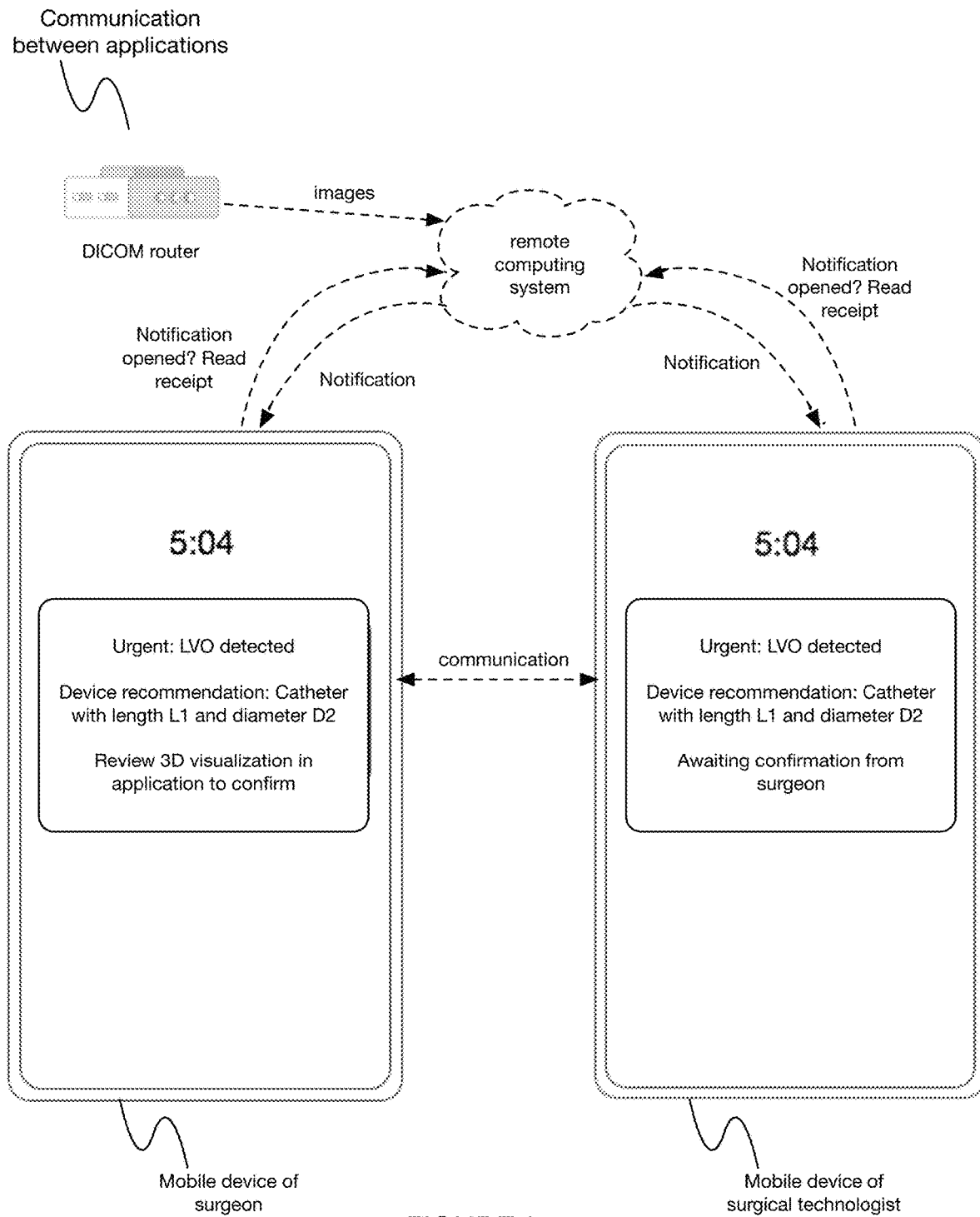
FIG. 3 is a schematic variation of a portion of the method for computer-aided decision guidance.

The system 100 can optionally include and/or interface with a computing and/or processing system 120, which functions to perform any or all of: receiving and processing data packets (e.g., dataset from router), interfacing with a user device (e.g., mobile device), removing metadata from a data packet (e.g., to comply with a regulatory agency), determining a set of notifications and/or alerts to send to users, triggering the set of notifications and/or alerts, establishing communication between multiple client applications (e.g., as shown in FIG. 3), and/or can perform any other suitable function(s).

The computing system and/or processing system can include a remote computing and/or processing system (e.g., cloud-based computing system), a local computing system (e.g., at a local server, onboard a mobile device or other device, etc.), or any combination.

In preferred variations, at least a portion of the method 200 is performed at a remote computing system (e.g., cloud-based), but additionally or alternatively any or all of the method 200 can be performed at a local computing system.

In some variations, the computing and/or processing system 120 provides an interface for technical support (e.g., for a client application) and/or analytics. Additionally or alternatively, the computing system can include storage configured to store and/or access a lookup table, wherein the lookup table functions to determine a treatment option (e.g., particular device), a user to automatically contact, a set of users to establish communication between, and/or any other suitable information. Additionally or alternatively, any or all of the information can be determined with artificial intelligence (AI), such as a with any or all of: a set of machine learning models and/or algorithms, a set of deep learning models and/or algorithms (e.g., neural networks, convolutional neural networks, etc.), a set of mappings, a decision tree, and/or with any other tools.

In some variations, the computing and/or processing system 120 connects multiple healthcare facilities and/or users (e.g., through a client application, through a messaging platform, etc.).

In some variations, the computing and/or processing system 120 functions to receive one or more inputs and/or to monitor a set of applications (e.g., executing on user devices, executing on workstations, etc.).

Additionally or alternatively, the computing and/or processing system can perform any other functions.

3.3 System—Application 130

The system 100 preferably includes and/or interfaces with one or more applications 130 (e.g., clients, client applications, client application executing on a device, etc.), which individually or collectively function to provide one or more outputs (e.g., from a remote computing system) to a user. Additionally or alternatively, the applications can individually or collectively function to receive one or more inputs from a user, provide one or more outputs to a healthcare facility (e.g., first point of care, second point of care, etc.) and/or a database associated with the healthcare facility (e.g., EMR, EHR, PACS, etc.), establish communication between users, send alerts and/or notifications to users, and/or perform any other suitable function.

As described above, the application can be partially or fully customized to users, groups, healthcare facilities, and/or any other entities. In preferred variations, for instance, the alerts and notifications can be configured based on any or all of: the user's schedule (e.g., on-call vs. not on-call), preferences (e.g., for notification frequency, alert triggering, etc.), and/or any other information.

The application is preferably configured to be executed on a user device, and further preferably a mobile user device (e.g., with any or all of the processing performed at a remote computing system such as a cloud-based computing system, with any or all of the processing performed at the mobile device, any combination, etc.) of the user, such as a phone, tablet, smart watch, laptop, personal computer, and/or any other user device. The user device can be personal user device of the user, a device owned by the healthcare facility, and/or any other device. The application can additionally or alternatively be configured to execute on any other devices, such as a workstation of the healthcare facility and/or any other devices. In specific examples, for instance, an application is executed on a mobile device with which the user can interact (e.g., for viewing images and/or reconstructions, for manipulating images and/or reconstructions, for communicating with other users, for receiving user inputs, etc.), wherein processing associated with the application is preferably performed at least partially at a cloud-based computing system. Additionally or alternatively, any or all of the processing can be performed at the mobile device, at a local server, at a data collection device, at any combination of devices, and/or at any other locations.

In some variations, one or more features of the application (e.g., appearance, information content, information displayed, user interface, graphical user interface, etc.) are determined based on any or all of: the type of device that the application is operating on (e.g., user device vs. healthcare facility device, mobile device vs. stationary device), where the device is located (e.g., $1^{st}$ point of care, $2^{nd}$ point of care, etc.), who is interacting with the application (e.g., user identifier, user security clearance, user permission, etc.), or any other characteristic. In some variations, for instance, an application executing on a healthcare facility device will display a $1^{st}$ set of information (e.g., uncompressed images, metadata, etc.) while an application executing on a mobile user device will display a $2^{nd}$ set of information (e.g., compressed images, no metadata, etc.). In some variations, the type of data to display is determined based on any or all of: an application identifier, mobile device identifier, workstation identifier, or any other suitable identifier.

The application is preferably in communication with the computing system, but can additionally or alternatively be in communication with a router and/or any other suitable system components. The application preferably includes and/or interfaces with both front-end (e.g., application executing on a user device, application executing on a workstation, etc.) and back-end components (e.g., software, processing at a remote computing system, etc.), but can additionally or alternatively include just front-end or back-end components, or any number of components implemented at any suitable system(s).

The outputs provided by the application can include any or all of: an alert or notification (e.g., push notification, text message, call, email, etc.); an image set (e.g., compressed version of images taken at scanner, preview of images taken at scanner, images taken at scanner, etc.); a modeled set of images (e.g., as produced in S220); a set of tools for interacting with the image set, such as any or all of panning, zooming, rotating, adjusting window level and width, scrolling, performing maximum intensity projection [MIP] (e.g., option to select the slab thickness of a MIP), changing the orientation of a 3D scan (e.g., changing between axial, coronal, and sagittal views, freestyle orientation change), showing multiple views of a set of images; a worklist (e.g., list of patients presenting for and/or requiring care, patients being taken care of by specialist, patients recommended to specialist, procedures to be performed by specialist, etc.); a set of patient lists (e.g., as described below); a messaging platform (e.g., HIPAA-compliant messaging platform, texting platform, video messaging, group messaging etc.); a telecommunication platform (e.g., video conferencing platform); a directory of contact information (e.g., $1^{st}$ point of care contact info, $2^{nd}$ point of care contact info, etc.); tracking of a workflow or activity (e.g., real-time or near real-time updates of patient status/workflow/etc.); analytics based on or related to the tracking (e.g., predictive analytics such as predicted time remaining in radiology workflow or predicted time until stroke reaches a certain severity; average time in a workflow; average time to transition to a second point of care, etc.); resources and/or content (e.g., digital handbooks with device specifications and/or instructions for reference); or any other suitable output.

The inputs received at the application can include any or all of the outputs described previously, touch inputs (e.g., received at a touch-sensitive surface), audio inputs, optical inputs, or any other suitable input. The set of inputs preferably includes an input indicating receipt of an output by a recipient (e.g., read receipt of a specialist upon opening a notification). This can include an active input from the user (e.g., contact user selection at application), a passive input (e.g., read receipt), or any other input.

In some variations, the application at least partially functions as a mobile PACS viewer, which enables user to view the images and any or all other information associated with the patient and included in PACS. Additionally or alternatively, the application can include any other information (e.g., non-PACS patient information, other user information, healthcare facility information, etc.), a server other than PACS can be integrated, and/or the application can have any other functions.

The application preferably includes and/or interfaces with a communication platform including a messaging platform, which functions to enable communication between multiple users and/or between users and entities (e.g., databases, healthcare facility administrators, technical support, etc.). The messaging platform is preferably a secure platform configured to be compliant with healthcare regulations (e.g., Health Insurance Portability and Accountability Act [HIPAA]) and/or any other privacy and/or data security protocols (e.g., encryption protocols).

The messaging platform preferably enables messages (equivalently referred to herein as chats) to be exchanged between users. The communication platform can additionally or alternatively include voice communications (e.g., with a Voice over Internet Protocol [VoIP]), which can function in some cases to still enable communication even when a user loses connection; video communications (e.g., teleconferencing, video consultations, video communications with a sales representative for advice during a procedure, etc.); and/or any other communications. The messaging platform is preferably part of the application, but can additionally or alternatively be a $3^{rd}$ party application in communication with the application, a native application to the mobile device (e.g., text messaging application), and/or any other application.

In one variation, the system 100 includes a mobile device application 130 and a workstation application 130—both in communication with the computing system—wherein a shared user identifier (e.g., specialist account, user account, etc.) can be used to connect the applications (e.g., retrieve a case, image set, etc.) and determine the information to be displayed at each application (e.g., variations of image datasets). In one example, the information to be displayed (e.g., compressed images, high-resolution images, etc.) can be determined based on: the system type (e.g., mobile device, workstation), the application type (e.g., mobile device application, workstation application,), the user account (e.g., permissions, etc.), any other suitable information, or otherwise determined.

The application can include and/or interface with any suitable algorithms or models (e.g., AI models, machine learning models, deep learning models, etc.) for analysis (e.g., at a computing and/or processing system, retrieved from storage, retrieved from remote storage, etc.), and part or all of the method 200 can be performed by a processor associated with the application. The algorithms and/or models can include AI models and/or algorithms, non-AI models and/or algorithms (e.g., programmed models), or any combination. In some variations, for instance, a set of AI models is used to process the set of images in order to determine a suspected condition, such as described in any or all of: U.S. application Ser. No. 16/012,458, filed 19 Jun. 2018, U.S. application Ser. No. 16/012,495, filed 19 Jun. 2018, U.S. application Ser. No. 16/913,754, filed 26 Jun. 2020, U.S. application Ser. No. 16/938,598, filed 24 Jul. 2020, U.S. application Ser. No. 17/001,218, filed 24 Aug. 2020, U.S. application Ser. No. 16/688,721, filed 19 Nov. 2019, and U.S. application Ser. No. 17/385,326, filed 26 Jul. 2021, each of which is incorporated in its entirety by this reference. One or more AI models and/or algorithms can additionally or alternatively function to implement any or all of the processes described below, such as determining which users to establish communication between (e.g., based on a prediction of which treatment group a patient will require based on a suspected condition), determining a care team for the patient, selecting a procedure and/or medical device for the patient, and/or any other processes.

Additionally or alternatively, the application can be configured for any or all of: case sharing, actionable alerts and notifications sent to users, integrations with $3^{rd}$ party applications and/or systems, and/or any other actions.

3.4 System—Additional Components

The system 100 and/or or any component of the system 100 can optionally include or be coupled to any suitable component for operation, such as, but not limited to: a processing module (e.g., processor, microprocessor, etc.), control module (e.g., controller, microcontroller), power module (e.g., power source, battery, rechargeable battery, mains power, inductive charger, etc.), sensor system (e.g., optical sensor, camera, microphone, motion sensor, location sensor, etc.), or any other suitable components.

4. Method

As shown in FIG. 2, a method 200 for computer-aided decision guidance includes: receiving a set of data S210; determining a set of parameters associated with the set of data S230; and triggering an output based on the set of parameters S230. Additionally or alternatively, the method 200 can include analyzing the set of data S220 and/or any other suitable processes performed in any suitable order.

Further additionally or alternatively, the method can include any or all of the methods, processes, embodiments, and/or examples as described in U.S. application Ser. No. 16/012,458, filed 19 Jun. 2018, U.S. application Ser. No. 16/012,495, filed 19 Jun. 2018, U.S. application Ser. No. 16/913,754, filed 26 Jun. 2020, U.S. application Ser. No. 16/938,598, filed 24 Jul. 2020, U.S. application Ser. No. 17/001,218, filed 24 Aug. 2020, and U.S. application Ser. No. 16/688,721, filed 19 Nov. 2019, and U.S. application Ser. No. 17/385,326, filed 26 Jul. 2021, each of which is incorporated in its entirety by this reference, or any other suitable processes performed in any suitable order. The method 200 can be performed with a system as described above and/or any other suitable system.

The method 200 can be performed with a system 100 as described above and/or with any other suitable system.

The method 200 preferably functions to assist physicians in preparing and/or planning for care (e.g., surgical treatment, pharmaceutical treatment, long-term care planning, etc.) of a patient, such as providing information and/or making recommendations related to any or all of: an optimal set of devices with which to perform a surgery, an optimal path to take during a surgical procedure (e.g., optimal vasculature path and/or point of entry), an optimal surgical team to assemble, a selection of medication for the patient, a selection of medication versus surgical treatment for the patient, a determination of whether or not to intervene, a determination of when to intervene, and/or can provide any other information and/or recommendations. Additionally or alternatively, the method 200 can function to provide one or more mobile tools (e.g., 3D viewers, messaging platforms, etc.) with which physicians (e.g., surgeons) and/or other care team members (e.g., surgical technologists, nurses, etc.) can interact and/or communicate. Further additionally or alternatively, the method 200 can perform any other function(s).

In preferred variations, the method 200 is used in cases of patients presenting with acute and/or otherwise time-sensitive conditions, such as cases of stroke (e.g., ischemic stroke, hemorrhagic stroke, etc.). Additionally or alternatively, the method 200 can be implemented in any other acute cases (e.g., cardiac events, trauma, emergency events, etc.), other brain conditions (e.g., aneurysms), and/or in any other health events associated with a patient.

4.1 Method—Receiving a Set of Data S210

The method 200 can include receiving a set of data S210, which functions to receive information with which to perform any or all of the remaining processes of the method 200. Additionally or alternatively, S210 can function to trigger any or all of the processes described below, and/or S210 can perform any other functions.

S210 is preferably performed initially in the method 200 and optionally at multiple times during the method 200 (e.g., as incoming information is received, in response to a user request, in response to a user action, continuously, at a predetermined frequency, at random intervals, at different times for different types of data, etc.). Additionally or alternatively, S210 can be performed at any other times and/or the method 200 can be performed in absence of S210.

The set of data can include image data, non-image data (e.g., electrical signals, ECG/EKG signals, demographic information, historical information, etc.), any other data, and/or any combination of data.

In a first set of variations (e.g., involving stroke patients, involving patients experiencing a neurological condition, involving patients experiencing a cardiological condition, involving patients experiencing a lung pathology, involving patients experiencing trauma, etc.), the set of data includes a set of images, such as images taken at (e.g., sampled at, imaged by, etc.) an imaging modality (e.g., computed tomography [CT] scanner, magnetic resonance imaging [MRI] scanner, ultrasound scanner, etc.). Additionally, the set of data can further include non-image data (e.g., set of signals, demographic information, etc.) and/or any other data or combination of data.

In a second set of variations (e.g., involving patients experiencing a cardiological condition, involving patients experiencing a lung pathology, involving patients experiencing trauma, involving stroke patients, involving patients experiencing a neurological condition, etc.), the set of data includes non-image data (e.g., ECG/EKG signals). Additionally, the set of data can further include image data and/or any other data or combination of data.

The set of data is preferably received at a computing system from any or all of: a router, a set of applications (e.g., at multiple user devices), another computing system and/or database, and/or any other sources. Alternatively, the set of data can be received at any other locations from any suitable sources.

In variations in which the set of data includes a set of images, the set of images are preferably received from an imaging modality (e.g., scanner, CT scanner, MRI scanner, ultrasound imaging device, etc.), PACS or other server, a database (e.g., for historical patient images), and/or from any other sources. The imaging modalities can include, for instance, any or all of: x-ray, computed tomography (CT) (e.g., CT-angiography, ECG-gated CT angiography, etc.), magnetic resonance imaging (MRI), ultrasound, and/or any other modalities. In preferred variations (e.g., stroke), the set of images show a brain and/or a brain region of the user, but can additionally or alternatively be associated with any other anatomical regions. In additional or alternative variations, for instance, the set of images correspond to (e.g., depict) a cardiac region (e.g., heart, heart chambers, heart valves, cardio vasculature, etc.) of the user, a lung region of the user, an anatomical region experiencing trauma (e.g., broken or fractured bone, punctured lung, etc.) and/or any other region or combination of regions.

Optionally, any or all of the system and/or method can be optimized for one or more specific modalities. Additionally or alternatively, image data can be generated from a camera, user device, accessed from a database or web-based platform, drawn, sketched, or otherwise obtained. In a specific example, for instance, the image viewing tools are customized based on (e.g., optimized for) the particular imaging modality (e.g., X-ray vs. CT vs. MRI vs. ultrasound, etc.) associated with the set of images, such as any or all of the image manipulation tools. The images are preferably organized into studies, wherein the user can view a current study and further preferably can view any past studies. Additionally or alternatively, the user can be associated with any other viewing permissions and/or can view images organized in any other ways.

The set of inputs can additionally or alternatively include any other inputs, such as other patient information (e.g., medical history and/or medical records, preferences, demographic information, lifestyle information, etc.), healthcare facility information (e.g., specialties, departments, number of beds available, scheduling information, etc.), specialist information (e.g., preferences, specialty, procedures the specialist is qualified and/or certified to perform, procedures the specialist prefers performing and/or is most qualified performing, on-call schedule, etc.), device information (e.g., device handbooks, device specifications, device parameters such as size parameters, device inventory at a particular healthcare facility, etc.), device representative information (e.g., contact information, availability, location, etc.), and/or any other suitable information.

In some variations, for instance, S210 includes retrieving a set of inputs, such as retrieving historical information (e.g., prior imaging studies), demographic information, medical information (e.g., from medical records), and/or any other information associated with a patient (e.g., in response to receiving new image study for the patient).

The set of inputs can further additionally or alternatively include any inputs received from a user (e.g., specialist, device representative, etc.) at the application (e.g., as described above, as described below, etc.), inputs received from a database (e.g., EMR, EHR, etc.), and/or any other inputs.

In a preferred set of variations, S210 includes receiving a set of images for a patient from a scanner (e.g., from a router coupled to a scanner), wherein the set of images is received at a computing system (e.g., remote computing system, local computing system, etc.) for processing.

In another set of variations, S210 includes receiving a set of signals (e.g., ECG signals, heart rate signals, etc.) from a signal collection device (e.g., ECG signal collection device, heart rate monitor, blood pressure cuff, vital signs monitor, etc.).

Additionally or alternatively, S210 can include any other processes and/or be otherwise suitably performed.

4.2 Method—Analyzing the Set of Data S220

The method 200 can include analyzing the set of data S220, which preferably functions to enable the determination of a set of parameters associated with the set of data (e.g., in S230). Additionally or alternatively, analyzing the set of data can function to produce one or more visualizations with which a user can more clearly assess the images and/or plan for a surgery or other treatment. Further additionally or alternatively, S220 can perform any other functions.

Figure 5A:
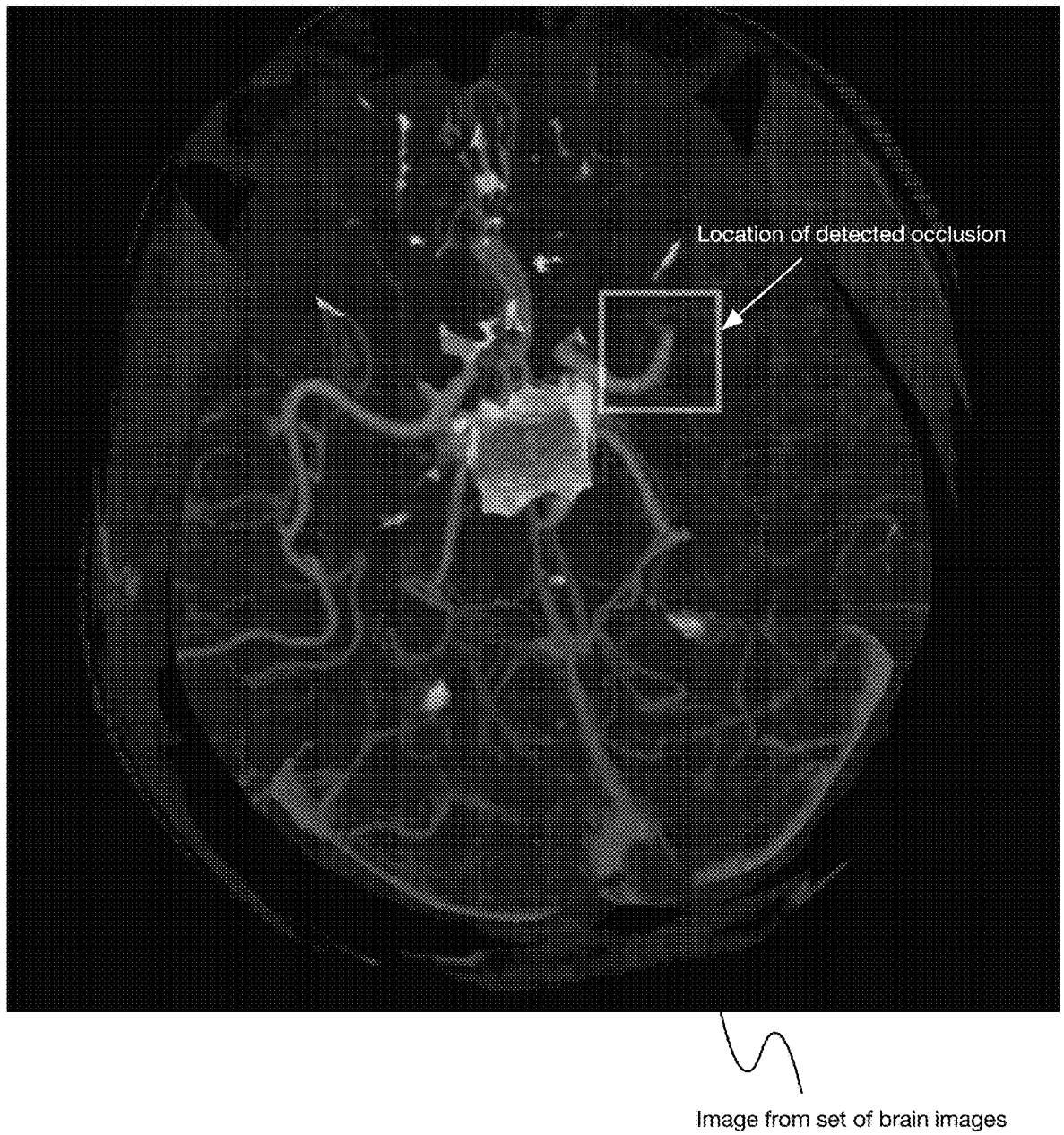
FIGS. 5A-5B depict a variation of a set of images along with a set of parameters used in the method for computer-aided decision guidance.
Figure 5B:
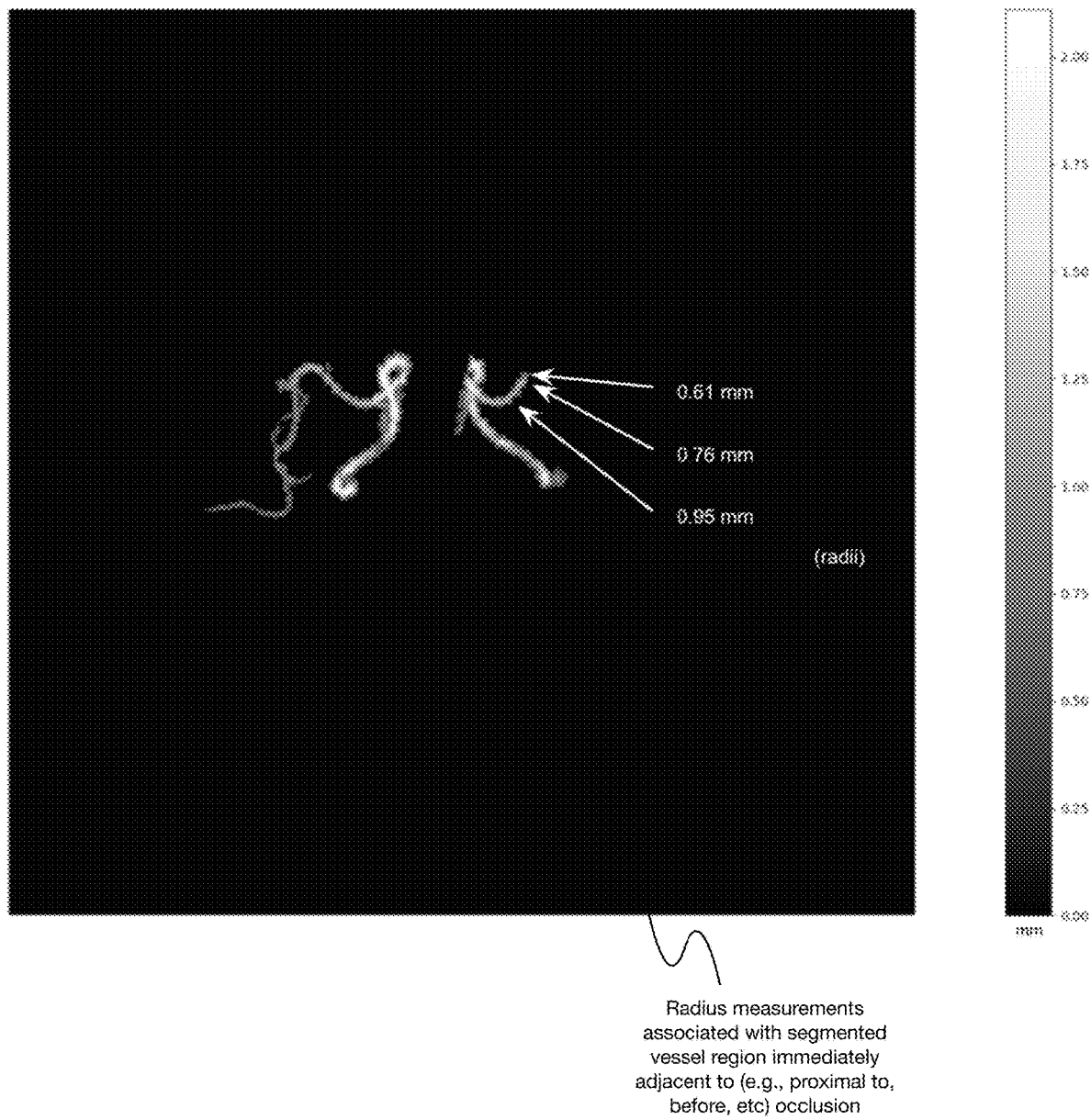
Figures 6A, 6B:
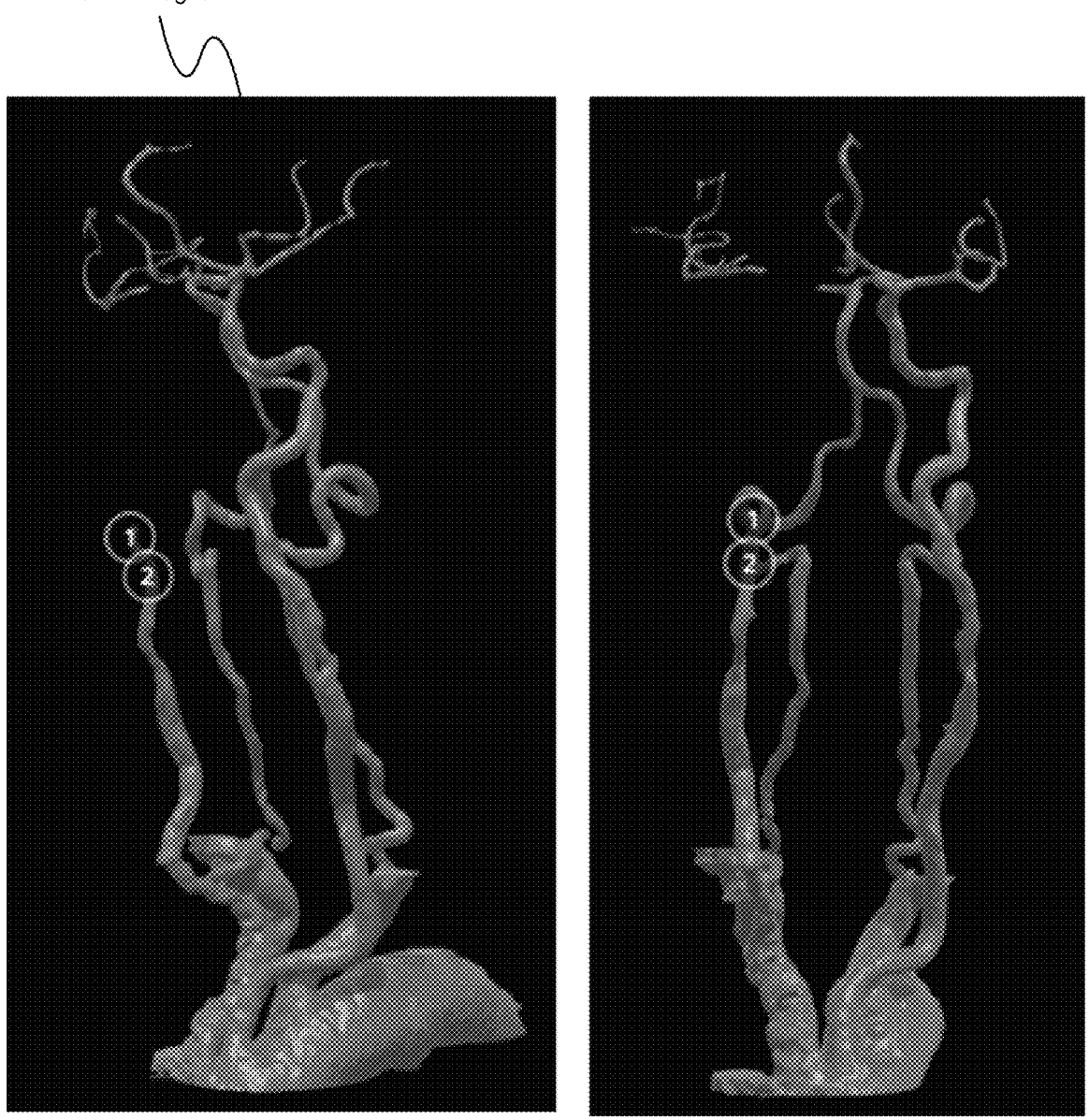
FIGS. 6A-6E depict a variation of a modeled set of images used in the method for computer-aided decision guidance.
Figure 6C:
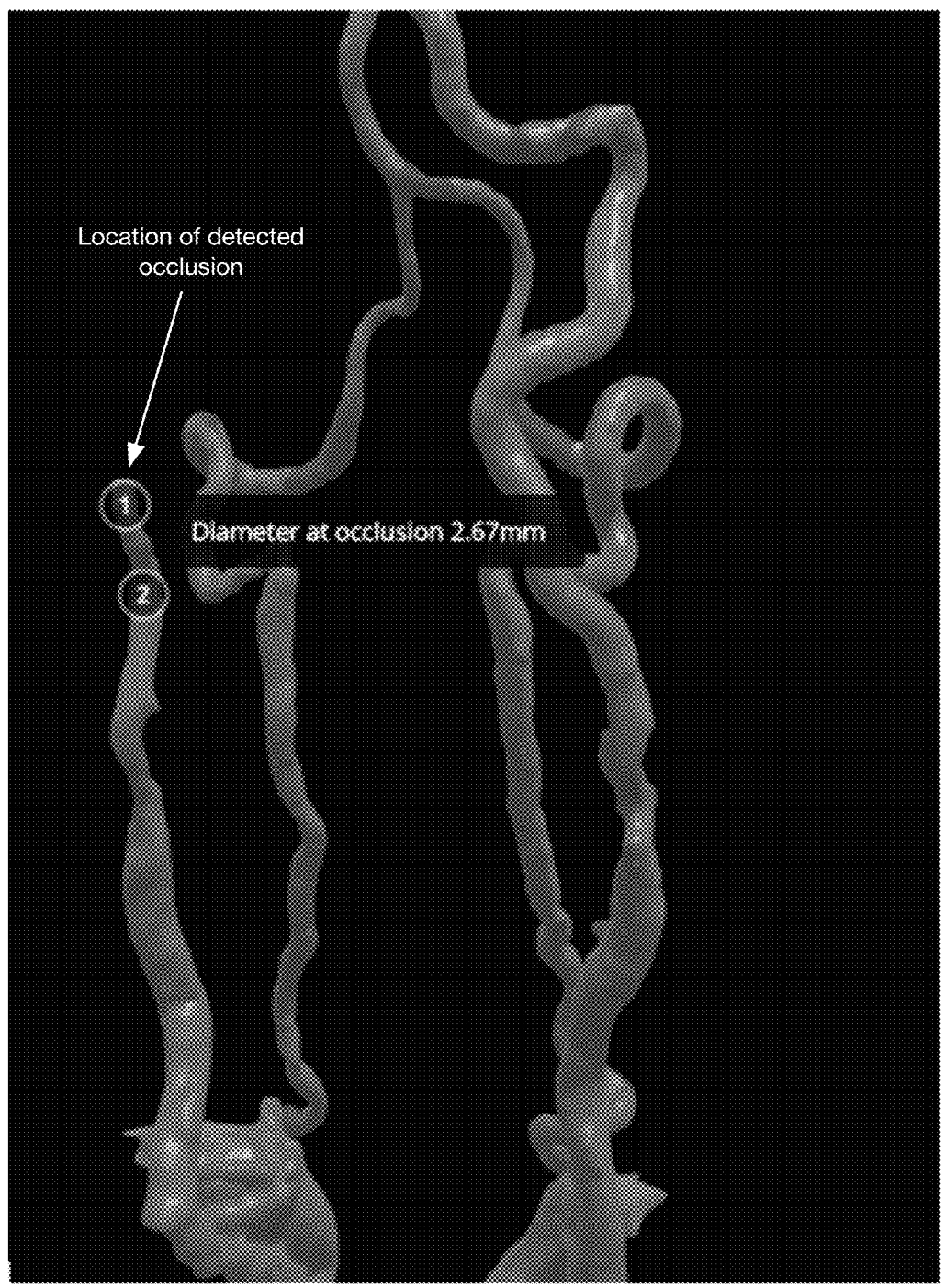
Figure 6D:
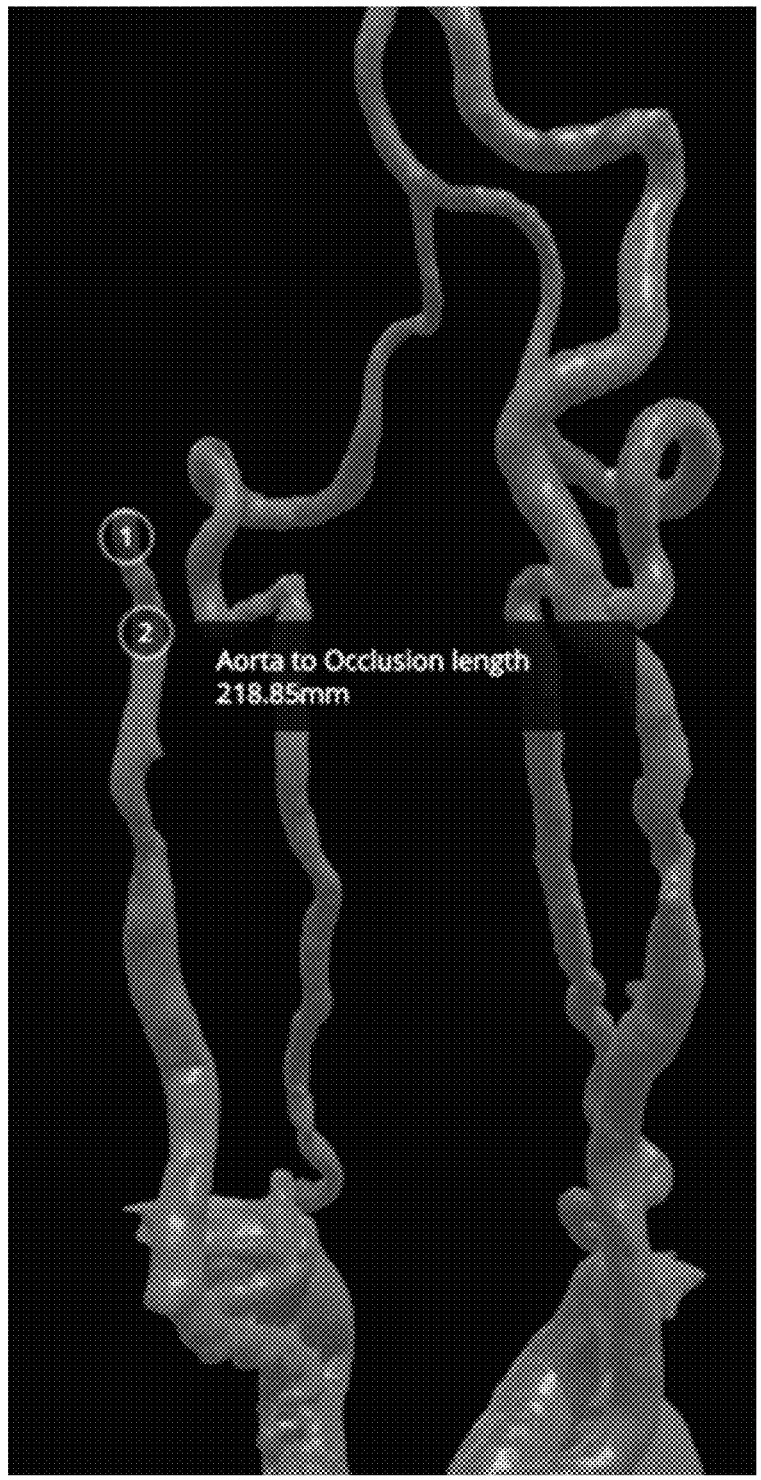
Figure 6E:
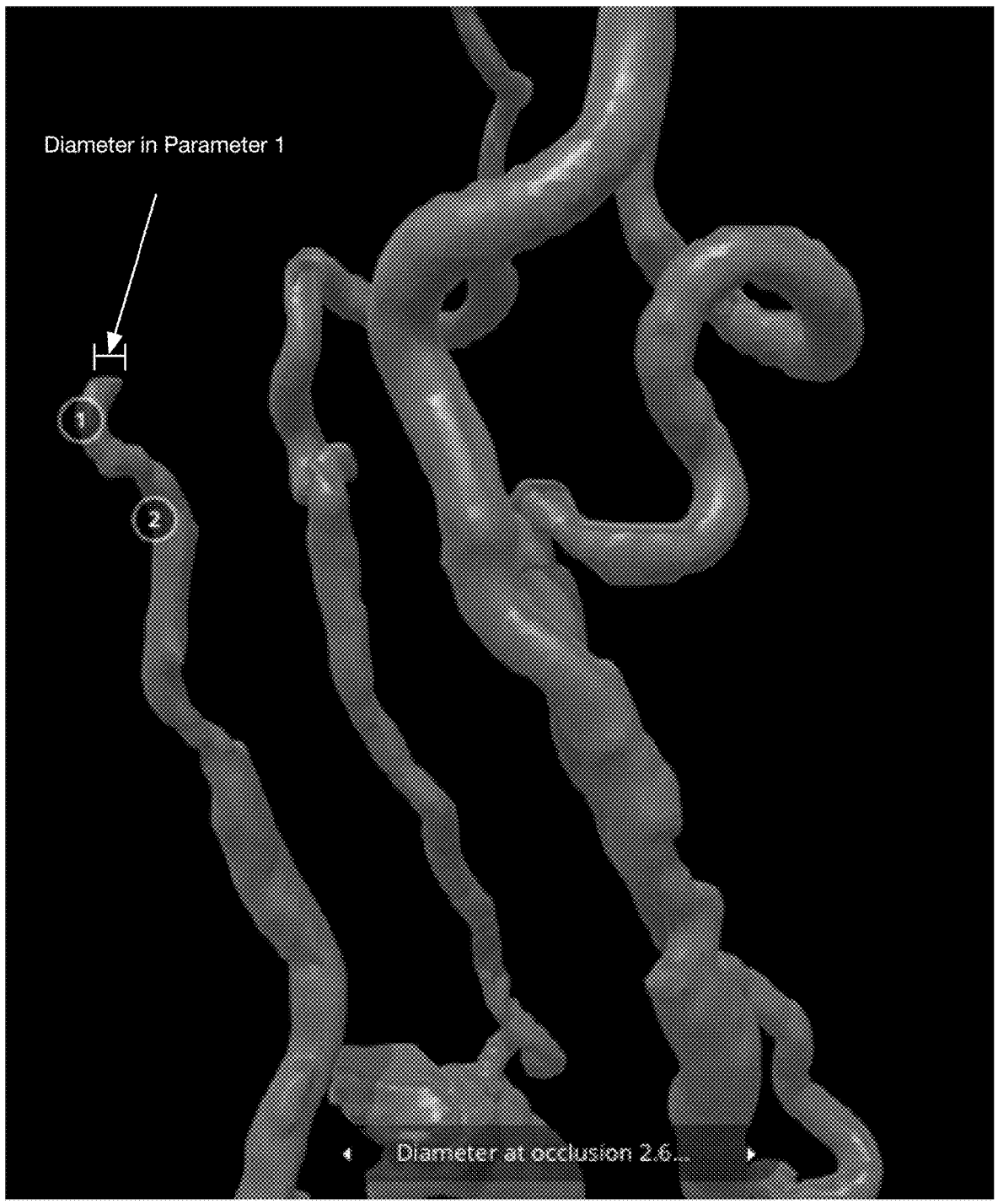

S220 is preferably performed in response to and based on S210, and optionally at multiple times during the method. Additionally or alternatively, S220 can be performed at any other times and/or the method 200 can be performed in absence of S220. Further additionally or alternatively, S220 can include and/or be performed in response to detecting a suspected condition associated with the set of data (e.g., as shown in a detected suspected LVO in a set of images as shown in FIGS. 5A-5B). In a first set of variations, for instance, S220 is performed in response to detecting an acute condition, such as, but not limited to, any or all of: a brain event (e.g., an ischemic stroke such as a large vessel occlusion [LVO], a hemorrhagic stroke, etc.), a respiratory event (e.g., pulmonary embolism), a cardiac event (e.g., heart attack), and/or any other event. The suspected condition is preferably determined automatically, such as a with a set of trained models (e.g., machine learning models, deep learning models, etc.), but can additionally or alternatively be determined manually (e.g., by a radiologist), any combination, and/or otherwise determined.

In specific examples, for instance, S220 is performed in response to detecting a suspected condition as described in any or all of: U.S. application Ser. No. 16/012,458, filed 19 Jun. 2018, U.S. application Ser. No. 16/012,495, filed 19 Jun. 2018, U.S. application Ser. No. 16/913,754, filed 26 Jun. 2020, U.S. application Ser. No. 16/938,598, filed 24 Jul. 2020, U.S. application Ser. No. 17/001,218, filed 24 Aug. 2020, U.S. application Ser. No. 16/688,721, filed 19 Nov. 2019, and U.S. application Ser. No. 17/385,326, filed 26 Jul. 2021, each of which is incorporated herein in its entirety by this reference.

S220 can be performed with any or all of: a set of models and/or algorithms (e.g., trained models, machine learning models, deep learning models, etc.), a set of rule-based processes, a set of segmentation processes (e.g., with segmentation software, with $3^{rd}$ party software, etc.), a set of decision trees and/or lookup tables, and/or any other processes.

S220 is preferably performed within a predetermined time period, wherein performing S220 within the predetermined time period is configured to enable the user to plan for care (e.g., surgery) of the patient without significantly delaying his or her treatment. This time period can be any or all of: less than the time conventionally required to model a set of diagnostic images, less than a threshold time period (e.g., 1 minute, 30 seconds, 10 seconds, 5 seconds, less than 5 minutes, between 0 seconds and 2 minutes, less than 10 minutes, etc.), and/or any other time period. Additionally or alternatively, S220 can be performed in accordance with any other features or parameters.

In variations in which the set of data includes a set of images, S220 preferably includes modeling the set of images. Modeling the set of images preferably includes determining a three-dimensional (3D) representation (e.g., 3D visualization, 3D reconstruction, etc.) based on a set of two-dimensional (2D) images received in S210 (e.g., as shown in FIGS. 6A-6E, etc.). The 3D representation is preferably performed with a set of one or more segmentation processes, but can additionally or alternatively be performed with any other processes.

Additionally or alternatively, S220 can include annotating any or all of the set of images (e.g., to efficiently indicate particular regions to a user, to convey measurements and/or parameters associated with a suspected pathological condition and/or anatomical region, to indicate a potential and/or recommended surgical pathway, etc.) and/or any other processes.

In variations in which the set of data includes non-image data, such as a set of signals, S220 can include a set of signal analysis processes. At least a portion of the signal analysis processes is preferably performed with a set of trained models and/or algorithms, but can additionally or alternatively be performed with a set of rule-based models and/or algorithms, manual processes, and/or any other tools or processes.

S220 can optionally include presenting the modeled set of images and/or any other intermediate outputs associated with the set of data to a user, wherein a user preferably refers to a physician (e.g., surgeon, primary care physician, emergency doctor, neuro interventionalist, etc.) and/or any other care team members (e.g., nurse, surgical technologist, etc.) involved in the care of the patient. Additionally or alternatively, the users can include any or all of: medical device sales representatives (e.g., involved in the selection and/or recommendation of a medical device for surgery), clinical trial representative (e.g., involved in the recruitment of patients for a clinical trial), and/or any other individuals involved in the care and/or planning of care for the patient.

In some examples, for instance, S220 includes presenting a 3D visualization associated with the set of images received in S210 to users (equivalently referred to herein as a recipients) at a client application executing on a mobile device associated with the user, wherein the 3D visualization can optionally be manipulatable (e.g., rotatable, scalable, etc.) and/or otherwise interacted with by the user. Additionally or alternatively, the 3D visualization can be viewable at other devices (e.g., a workstation at the healthcare facility), a 2D visualization (e.g., one or more 2D images which depict evidence of the suspected pathology, a single image which depicts a most severe view of the suspected pathology such as an image which depicts a largest diameter of a large vessel occlusion, etc.), and/or otherwise presented to the user.

Additionally or alternatively, S220 can include any other processes.

4.3 Method—Determining a Set of Parameters Associated with the Set of Data S230

The method 200 can include determining a set of parameters associated with the set of data S230, which functions to determine information which care providers (e.g., specialists) can use in performing decision-making for care of the patient. This can enable, for instance, any or all of: the selection of an optimal medical device to be used in surgery, the selection of an optimal (e.g., most efficacious) drug, the selection of an optimal type of surgery, the determination of an optimal path and/or entry point for a surgical intervention, and/or can enable any other outcomes.

S230 is preferably performed in response to and based on S220, and optionally at multiple times during the method. Additionally or alternatively, S230 can be performed during S220 and/or in parallel with S220, at any other times during the method 200, in absence of S220, and/or the method 200 can be performed in absence of S230.

The set of parameters is preferably determined based on one or more outcomes (e.g., modeled set of images, processed set of signals, etc.) produced in S220, but can additionally or alternatively be determined in absence of S220, and/or based on any other information.

The set of parameters is preferably at least partially determined automatically, such as with a set of models (e.g., trained models, machine learning models, deep learning models, etc.) and/or algorithms (e.g., as utilized in S220), but can additionally or alternatively be determined based on a set of manual processes, and/or with any combination of processes.

The set of parameters preferably includes one or more geometric features associated with the set of images, such as any or all of: dimensions (e.g., lengths, diameters, curvatures, radii, etc.), volumes, surface areas, and/or any other geometric features associated with the anatomical region(s) associated with the set of images.

The parameters can be associated with (e.g., characterize, define, etc.) any or all of: a pathological region and/or feature (e.g., clot size, aneurysm size, fracture location, etc.); a non-pathological region and/or feature (e.g., vessel diameter proximal to a detected occlusion, vessel diameter of a vessel needed to access an occlusion and/or aneurysm, etc.); any other regions or features; and/or any combination of regions or features.

In variations involving vasculature, such as vessels in the brain, the set of parameters can include, for instance, one or more vessel diameters, such as any or all of: a vessel diameter immediately before (e.g., proximal and adjacent to) an occlusion or other landmark (e.g., along a path that the surgeon would take with a catheter); a diameter of the narrowest part of a vessel needed to reach the occlusion or other landmark; a total length of the vessels needed to reach the occlusion or other landmark; one or more parameters associated with the tortuosity of the vessels (e.g., sharpest angle along a proposed path for reaching an occlusion, average tortuosity of the vessel(s), etc.); and/or any other parameters. Additionally or alternatively, any other features associated with vasculature can be detected, such as vessel calcification (e.g., presence of calcification, amount of calcification, location of calcification, severity of calcification, etc.) and/or any other features.

In specific examples involving a vessel occlusion (e.g., LVO), the set of parameters determined in S230 can include any or all of: a vessel diameter immediately before an occlusion based on a proposed vessel path to access the occlusion (e.g., with a catheter); diameters of the narrowest part(s) of the vessel(s) along the path and/or the diameter(s) associated with any major arteries such as the internal carotid artery [ICA], middle cerebral artery [MCA] (e.g., M1 segment of MCA, M2 segment of MCA, M3 segment of MCA, M4 segment of MCA, etc.), anterior cerebral artery [ACA], and/or any other arteries; optionally a total distance of the path (e.g., based on aggregating the vessel lengths); a tortuosity of the vessels; and/or any other parameters.

The set of parameters can additionally or alternatively include features associated with the suspected condition. For variations involving an occlusion such as a clot, the set of parameters can include, for instance, any or all of: a type and/or composition of a clot (e.g., white clot vs. red clot, a calcified clot, a fibrin-rich vs. a low-fibrin clot, a porosity of a clot, perviousness of a clot, permeability of a clot, etc.); one or more dimensions of a clot (e.g., diameter, length, largest dimension, volume, surface area, etc.); arrangement of a clot within a vessel (e.g., arranged in a straight portion of the vessel, arranged in a curve of the vessel, etc.); and/or any other features of the clot(s). Any or all of these parameters can optionally be determined based on intensity values (e.g., Hounsfield Unit [HU] values) associated with the set of images and/or any other information.

Figure 7:
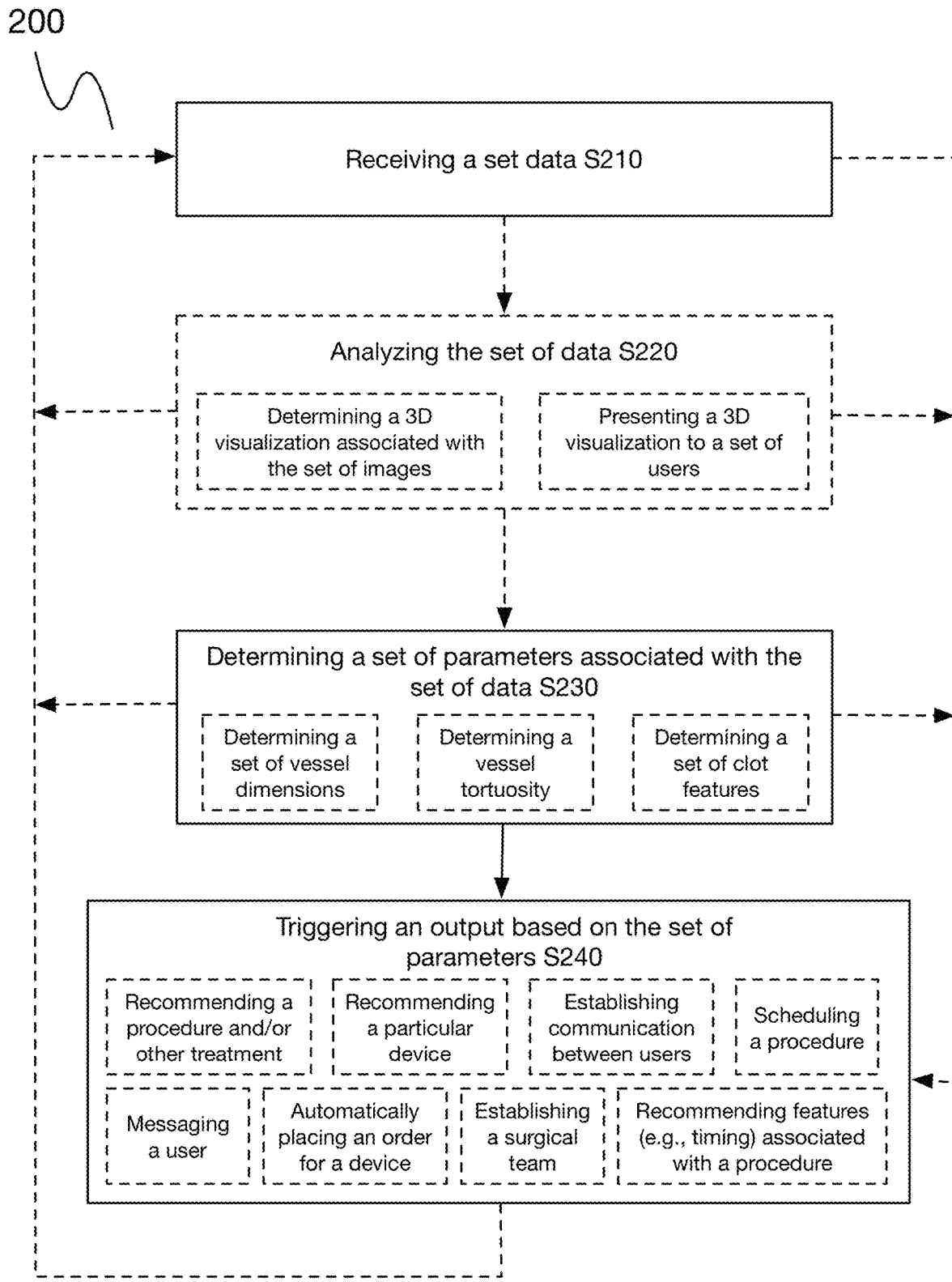
FIG. 7 depicts a schematic variation of the method for computer-aided decision guidance.

In a first set of variations involving a vessel occlusion (e.g., as shown in FIG. 7), S230 includes determining any or all of: a set of vessel diameter values (e.g., smallest diameter values), a set of clot parameters (e.g., white vs. red blood clot, calcification level of clot porosity of clot, etc.), and optionally any or all of a set of vessel lengths, other vessel parameters (e.g., tortuosity, maximum curvature, regions having a curvature above a predetermined threshold, diameter, etc.), and/or any other parameters.

In a set of specific examples (e.g., as shown in FIGS. 5A-5B), S230 includes determining at least a set of radii associated with a segmented vessel region, wherein the segmented vessel region is arranged immediately before the occlusion.

In another set of specific examples (e.g., as shown in FIGS. 6A-6E), S230 includes determining a diameter of the vessel immediately before the collusion; a length from an aorta to the occlusion; and optionally any other parameters.

Additional variations and types of parameters determined can include any or all of those described below.

Additionally or alternatively, S230 can include any other processes.

4.4 Method—Producing and/or Triggering an Output Based on the Set of Parameters S240

The method 200 can include producing and/or triggering an output based on the set of parameters S240, which functions to initiate and/or perform an action related to care of the patient. Additionally or alternatively, S240 can function to: initiate an action in less than a predetermined threshold of time; initiate an action with no and/or minimal user input; prevent the need to try multiple devices and/or treatment options for a patient; improve patient outcomes (e.g., by selecting an optimal device for surgery); and/or perform any other functions.

S240 is preferably performed in response to and based on S230, and optionally at multiple times during the method. Additionally or alternatively, S240 can be performed at any other times and/or the method 200 can be performed in absence of S240.

S240 is preferably performed with a computing system (e.g., as described above), further preferably with a set of one or more models (e.g., machine learning models) and/or algorithms, but can additionally or alternatively be performed with one or more databases, lookup tables, decision trees, and/or any other tools.

In preferred variations, at least a portion of the outputs are determined automatically, such as by a computing system (e.g., as described above). Additionally or alternatively, any or all of the outputs can be determined manually, partially automatically (e.g., automatically with user input), and/or any combination.

S240 can optionally include selecting (e.g., recommending, initiating, etc.) a type of procedure and/or other treatment option for the patient. In the case of an acute brain condition (e.g., stroke), for instance, this can include selecting: a procedure vs. medication-only treatment (e.g., tissue plasminogen activator [tPA]), a type of procedure (e.g., revascularization, clot retrieval, aspiration, catheter/microcatheter-based surgical intervention, meshing, stenting, aneurysm clipping, endovascular microcoil embolization, balloon-assisted coiling, etc.), and/or selecting any other care and/or features of care for the patient.

In variations in which a procedure (e.g., surgery) is going to be performed, S240 can optionally additionally or alternatively include selecting (e.g., recommending, initiating, etc.) a medical device for use in the procedure. This preferably functions to enable early and accurate decision making for which device(s) to use in treating the patient, as an early choice of a proper device can improve the safety and efficacy of the procedure, reduce time to intervention, reduce cost and waste, and/or can confer any other benefits.

Selecting the medical device can include any or all of: a type of medical device, features (e.g., size, material composition, features, etc.) of a medical device, and/or any other information. In some variations, for instance, S240 can include selecting any or all of: a catheter diameter (e.g., based on vessel diameter, based on smallest vessel diameter, based on vessel diameter immediately before the occlusion, etc.), a catheter length (e.g., based on path length, based on length of one or more vessels, etc.), a catheter material (e.g., catheter flexibility based on vessel tortuosity), a catheter type (e.g., twist end catheter, suction catheter, etc.), whether or not aspiration is involved in the procedure (e.g., based on calcification of clot), a device type (e.g., catheter, revascularization device, coil, braid, aspiration system, etc.), a determination of whether or not to perform a procedure (e.g., based on a size of a clot, based on a calcification of a clot, etc.), and/or any other features.

In specific examples, for instance, S240 can include selecting a diameter of a catheter that is as large as possible while being no larger than a diameter of the narrowest part of the vessel needed to pass through to access the clot.

In additional or alternative specific examples, S240 includes selecting a catheter based on other features of the patient's anatomy and/or pathology, such as, but not limited to: a length of the catheter (e.g., based on a proposed path and associated path length for reaching the clot, based on a proposed access point for inserting the catheter into the patient, etc.); a stiffness and/or flexibility of the catheter (e.g., based on a tortuosity of the vessels needed to be traversed to reach the clot); a wall thickness of the catheter (e.g., based on a tortuosity of the vessels needed to be traversed to reach the clot); a material of the catheter; and/or any other features.

S240 can optionally additionally or alternatively include determining (e.g., predicting, recommending, etc.) features of the surgical procedure, such as a recommended path to reach an occlusion, an optimal entry point (e.g., groin, wrist, etc.) with which to insert a catheter, and/or any other features. In some examples, for instance, S240 can include warning surgeons of features that may cause delays during a procedure, which can have significant benefits as the surgeon plans an approach with a catheter—as such, the surgeon can more successfully select a device, modify a device and/or device selection based on the path, and/or enable them to otherwise better prepare for a surgery. In other examples, S240 can include automatically determining an optimal path (e.g., ordered set of vessels) for the surgeon to take to reach an occlusion or other location—this can function, for instance, to enable any or all of: decreasing the time conventionally spent by the surgeon on path planning, selecting a path with minimal tortuosity and/or a path which has no curvature exceeding a predetermined threshold, selecting a path with minimal narrowing and/or calcification, and/or otherwise selecting path. In some instances, S240 can further include providing a visualization of this path, such as at a 3D visualization provided in S220 (e.g., as an annotation overlaid on the 3D visualization).

S240 can optionally additionally or alternatively include determining whether or not to provide medication (e.g., tPA) to the patient, selecting features (e.g., dosage, duration, etc.) of medication, and/or any other information. In specific examples, for instance, the porosity or perviousness of the clot can be used to predict the clot's response to tPA, wherein in an event that the clot's porosity is above a predetermined threshold, tPA can be prescribed and/or administered to the patient (e.g., with a surgical procedure, instead of a surgical procedure, in a smaller dosage than if the clot was less porous, etc.).

S240 can optionally additionally or alternatively include generating and/or transmitting a message (e.g., alert, notification, etc.) to one or more users. The message is preferably delivered at a client application executing at a mobile device of the user (e.g., as described above), but can additionally or alternatively be delivered to a stationary device (e.g., workstation) and/or any other device(s). This can function, for instance, to alert a surgeon to a patient coming in for care (e.g., to help him or her prep earlier and/or in a mobile setting such as on the way to the hospital), to inform a tech team (e.g., surgical technologists) to have a particular device (e.g., automatically determined, determined by a surgeon, etc.) ready for a procedure, and/or can perform any other function(s). The alert is preferably automatically generated and sent (e.g., based on a set of machine learning models, based on a lookup table, etc.), but can additionally or alternatively be manually generated or any combination.

In specific examples, for instance, the name and information associated with a recommended device can be messaged to any or all of: a surgeon, a surgical technologist, a medical device sales representative associated with the surgeon, and/or any other users.

S240 can optionally additionally or alternatively include establishing communication between two or more users, such as at the client application and/or at any other platforms (e.g., paging system, $3^{rd}$ party messaging system, text messaging platform, etc.). This can include, for instance, any or all of: automatically establishing a message thread between users, automatically calling a second user from a first user's mobile device, automatically paging a second user from a first user, and/or establishing communication in any other way(s). In some examples, for instance, S240 can establish communication between any or all of: a surgeon and a medical device sales representative; a surgeon and a surgical technologist; all members of surgical team; and/or any other members. In a specific example shown in FIG. 3, for instance, S240 can include establishing communication between a surgeon and a surgical technologist to coordinate on the selection of a medical device to be prepared and used in surgery.

S240 can optionally additionally or alternatively include triggering any other actions such as, but not limited to, any or all of: the automatic ordering of a medical device; the automatic assembly/assignment of a surgical team; the automatic scheduling of a surgery; the initiation of the transfer of the patient from a first point of care to a second point of care (e.g., comprehensive stroke center); and/or any other actions.

In some variations, for instance, S240 can include automatically referencing (e.g., checking) an inventory database associated with any or all of: a user (e.g., specialist), the patient (e.g., inventory associated with the healthcare facility at which the patient is currently located and/or en route to), a healthcare facility (e.g., healthcare facility at which a specialist is located, healthcare facility at which the patient is located, healthcare facility at which the patient will receive treatment, etc.), and/or any other inventory database. In a set of examples, referencing an inventory database can function to determine which devices are available for selection, such that an optimal device which is available based on the inventory database can be recommended and/or suggested to the user. In another set of examples, additional or alternative to the first, the inventory database can be referenced in response to determining an optimal device, wherein in an event that the optimal device is not present, a second action (e.g., recommending an alternative device and/or treatment option, contacting a device representative or inventory management entity to procure the device, etc.) can be triggered.

In a first variation, S240 includes automatically recommending a catheter for the removal of a clot, wherein the particular catheter is determined based on a set of vessel diameters (e.g., narrowest part of vessel; diameter immediately before the clot; diameters of vessels at the ICA, MCA, M2, etc.) and/or any other information. S240 can additionally include automatically messaging one or more users (e.g., at the client application) with this recommendation and/or automatically placing an order for the device.

Additionally or alternatively, S240 can include any other processes.

The method 200 can additionally or alternatively include any other processes, such as, but not limited to, any or all of: training and/or re-training (e.g., updating) any or all of a set of models (e.g., based on an outcome of a procedure performed based on an output from the method) and/or any other processes.

5. Variations

In a first variation, the system and/or method are configured for any or all of: checking for a suspected condition (e.g., stroke, large vessel occlusion, intracerebral hemorrhage [ICH], ischemic stroke, hemorrhagic stroke, cardiac condition, pulmonary condition, trauma, etc.) based on processing a set of diagnostic images with a set of trained models and/or algorithms; identifying and optionally reconstructing (e.g., with a set of segmentation processes) a region from the set of images (e.g., based on the set of trained models and/or algorithms); calculating a set of parameters associated with the region; optionally making a determination that a particular condition is suspected based on analyzing (e.g., comparing with a set of thresholds) a first subset of the set of parameters; based on any or all of the set of parameters (e.g., the first subset, another subset, etc.), automatically determining a treatment option (e.g., based on aggregated information from historical procedures performed for a corpus of patients with that particular condition and their associated outcomes, based on referencing a lookup table and/or database, with a trained model, etc.), where the treatment option can include any or all of: a recommended procedure, a recommended device for a procedure, recommended features of the device, a non-surgical treatment recommendation, a recommended healthcare facility for receiving treatment, and/or any other treatment options; optionally selecting a recipient (e.g., based on the pathological condition, based on an availability associated with the recipient, based on an availability and/or schedule associate with the recipient, based on a location of the patient and/or the recipient, etc.); and triggering one or more actions (e.g., notification at an application of the recipient which includes a treatment option recommendation, referencing an inventory database to check for availability of a recommended device, automatically establishing communication between a specialist and a medical device sales representative associated with a recommended device to decrease the time required for the specialist to obtain the recommended device, etc.) in response to determining the treatment option.

The method can additionally include checking for multiple potential conditions (e.g., in parallel with checking for the neurological condition, in series with checking for the neurological condition), where in response to detecting which (if any) of the potential conditions apply, the process to determine a treatment option is performed specifically for the that particular potential condition.

In a first set of examples, the method includes: receiving a set of (e.g., CT, CTA, etc.) images; processing the set of images with a set of trained (e.g., machine learning, deep learning, etc.) models and/or algorithms to segment a set of vessels from the set of images; analyzing the segmented vessels to determine a set of diameters associated with the segmented vessels and/or any other regions associated with the images; comparing a portion of these set of diameters (e.g., those corresponding to a vessel obstruction/occlusion) with a set of thresholds to determine if a suspected neurological condition (e.g., large vessel occlusion, stroke, ischemic stroke, hemorrhagic stroke, etc.) is present and/or which particular neurological condition is suspected; in response to determining that a neurological condition is suspected, analyzing a second portion of diameters (e.g., different than the first portion, same as the first portion, overlapping with the first portion, etc.) outside of the pathology (e.g., vessel diameter immediately proximal to the obstruction, vessel diameter of the narrowest vessel in an approach path to reaching the obstruction, etc.) to select a recommended device (e.g., catheter having a largest possible diameter while being smaller than the narrowest vessel, catheter having a largest possible diameter while being smaller than the vessel diameter immediately proximal the obstruction, etc.) (e.g., referencing a database of available catheter [e.g., based on current inventory, absent of current inventory information, etc.] sizes); selecting a specialist associated with treatment of the suspected condition and/or the patient; transmitting a notification to the specialist and optionally any other recipients (e.g., medical device sales representative, surgical technician, inventory manager, etc.) with information regarding the recommended device (e.g., model number, features, etc.); and optionally triggering any other actions (e.g., establishing communication between individuals in response to the specialist accepting and/or overriding a recommended device, recommending a second recommended device in response to the first recommended device not being present in local inventory, contacting a second specialist in an event that the first specialist does not respond within a predetermined time threshold, etc.).

In a second set of examples, additional or alternative to recommending a particular device, the method includes automatically determining and/or recommending other features of a treatment and/or care of the patient, such as, but not limited to: a category of devices and/or procedures; a non-surgical intervention (e.g., medication recommendation, Tissue Plasminogen Activator [tPA] administration, etc.); a location at which to intervene and/or deploy devices; a timing of any or all procedures; a specialist for performance of the procedure; a healthcare facility at which a procedure is to be performed; and/or any other features.

In a third set of examples, in which a suspected aneurysm is detected, for instance, the method can include (additional or alternative to any of the processes described above) recommending a particular type of procedure and/or associated device (e.g., based on a size of the suspected aneurysm, based on a location of the suspected aneurysm, based on a proximity of the suspected aneurysm to other vessel anatomy, etc.), such as, for instance: a coiling of a suspected aneurysm (and optionally a particular coil recommendation such as a coil packing density, coil size, etc.) versus deploying an intrasaccular flow disruptor (e.g., braided-wire device, WEB device, self-expanding device etc.) (e.g., upon determining that the suspected aneurysm is located at an arterial bifurcation) (and optionally a particular intrasaccular flow disruptor device) versus deploying a flow diverting stent (and optionally a particular flow diverting stent [e.g., stent size, stent shape, etc.] and/or location).

In a fourth set of examples, in which a suspected clot and/or vessel occlusion is detected (e.g., based on brain images, based on cardiac images, etc.), for instance, the method can include (additional or alternative to any of the processes described above) automatically determining a recommendation of any or all of: a procedure type and/or types (e.g., balloon angioplasty, stent deployment, stent deployment with balloon angioplasty, etc.); a device type; a non-surgical intervention (e.g., tPA); a combination of surgical and non-surgical interventions; a timing of treatments; and/or any other recommendations. The recommendation is preferably determined based at least on an analysis of a set of images (e.g., CT images), such as based on any or all of: a location of the clot, the patient's vessel anatomy (e.g., location of occlusion relative to vessel bifurcations, vessel diameters, how close the occlusion is to the patient's carotid artery, etc.), features of the clot (e.g., level of calcification, porosity, etc.), blood flow information (e.g., flow rates proximal to occlusion), and/or any other features.

In a fifth set of examples, in which a suspected subdural hematoma is detected (e.g., based on brain images), for instance, the method can include (additional or alternative to any of the processes described above) analyzing (e.g., with a set of AI algorithms and/or models) a set of images to recommend one or more of: an endoscopic procedure to block off (e.g., with glue) one or more vessels contributing to the subdural hematoma; a craniotomy; a burr hole procedure; a lack of surgical intervention (e.g., monitoring for changes); and/or any other next steps. In particular examples, for instance, the set of models and/or algorithms locate and examine a particular artery and/or vasculature (e.g., middle meningeal artery), such as a vasculature involved in reducing a rebleeding rate, in order to make a recommendation. Additionally or alternatively, any or all of the following can be used in making a recommendation: a diameter of a bleed, a volume of a bleed, whether or not (and/or to what extent) a midline shift is present, and/or any other features.

In a sixth set of examples, in which a suspected hemorrhage (e.g., intracerebral hemorrhage [ICH]) is detected, for instance, a particular procedure (e.g., open surgery, minimally invasive surgery, endoscopic procedure), an associated device, a non-surgical intervention, and/or any other treatment decisions can be automatically made based on any or all of: a size of bleed, a location of a bleed, and/or any other features.

In a seventh set of examples, in which cardiac valve disease, for instance, is suspected/detected (e.g., based on analysis of an echocardiogram), the method can (additional or alternative to any of the processes described above) determine whether or not to recommend the insertion of a valve and optionally which valve (e.g., size, type, shape, location, etc.) to recommend based on any or all of: evidence of mitral regurgitation, evidence of aortic stenosis, blood flow rates, and/or any other features.

In an eighth set of examples, in which X-ray data is analyzed, bone trauma (e.g., fracture, breakage, etc.) can be detected and a recommendation made which informs treatment (e.g., which spinal vertebra is damaged, which devices [e.g., plates, screws, casts, etc.] should be implemented, etc.).

In a second variation, additional or alternative to the first, non-image data is analyzed and used in making any or all recommendations.

In a set of examples, for instance, a set of ECG signals are analyzed (e.g., with a set of models and/or algorithms) to detect whether a cardiac condition (e.g., hypertrophic cardiomyopathy [HCM]) is suspected, with treatment options and/or features (e.g., intervention, timing intervention, etc.) optionally recommended.

Figure 8:
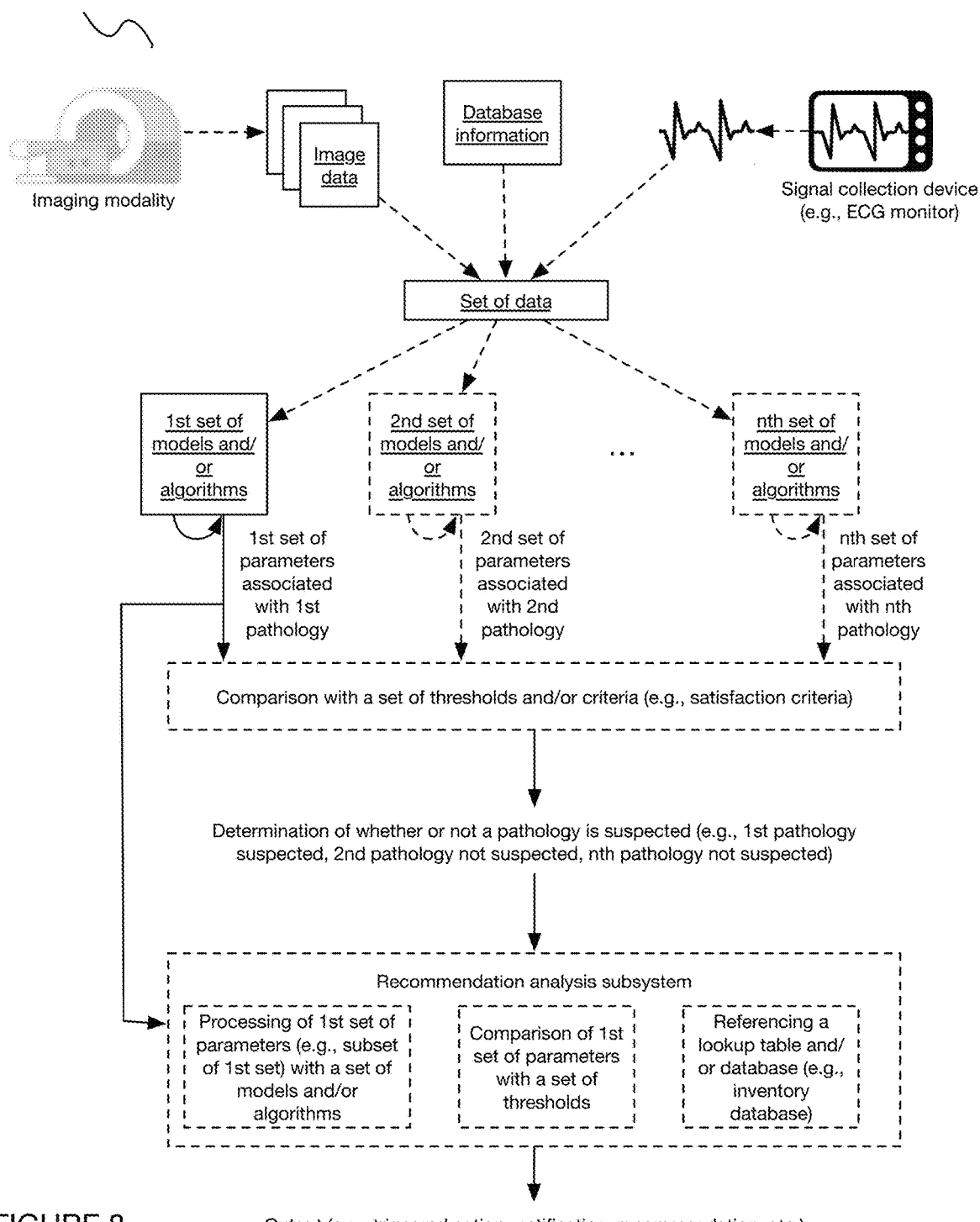
FIG. 8 depicts a schematic variation of information flow within a system and method for computer-aided decision guidance.

In a third variation (e.g., as shown in FIG. 8), additional or alternative to those described above, the method can include any or all of: receiving a set of data (e.g., image data, signal data, database information such as historical patient information and/or inventory information and/or specialist information, etc.); processing the data with one or more sets of models and/or algorithms, each of the sets of models and/or algorithms associated with a particular pathology/condition (e.g., large vessel occlusion, intracerebral hemorrhage, subdural hematoma, etc.) and/or category of pathologies/conditions (e.g., neural conditions, cardiac conditions, pulmonary conditions, etc.); producing a set of parameters with each of the set of models and/or algorithms; for each of the set of parameters, comparing a portion or all of the set of parameters with a set of thresholds to determine if an associated condition is suspected; if a condition is suspected, further processing (e.g., with a set of models and/or algorithms, with a set of rules and/or lookup tables and/or databases, etc.) any or all of the associated set of parameters (e.g., a different subset of parameters than those used to detect the suspected condition, a same subset of parameters as those used to detect the suspected condition, an overlapping subset with those used to detect the suspected condition, etc.) to determine a set of recommendations (e.g., recommended device and/or treatment for the pathology, recommended specialist to contact, etc.); and triggering one or more actions associated with the recommendation(s) (e.g., contacting a specialist with the recommended device, checking an inventory database to check if the recommended device is present, establishing communication between users, checking to see if a specialist accepts treatment and/or the recommendation and if the specialist does not respond within a predetermined threshold alerting a second specialist, etc.).

In a first set of examples, the sets of models and/or algorithms to be used in checking for a set of suspected conditions can be selected based on features in the set of data, such as, but not limited to, a type of image data (e.g., CT vs. MRI vs. ultrasound), metadata associated with the image data (e.g., indicating the anatomical region being imaged such that pathologies associated with that anatomical region are considered), historical information associated with the patient (e.g., previous conditions diagnosed for the patient, clinical notes of conditions being monitored, etc.), demographic information associated with the patient, type of data (e.g., ECG signal data triggers consideration of cardiac conditions), and/or any other features.

In a second set of examples, additional or alternative to the first, a first subset of parameters associated with a pathological region (e.g., segmentation which includes a pathology) is used to determine if a suspected condition is present, and a second subset of parameters associated with a non-pathological region (e.g., reconstructed vessels proximal to a pathology [e.g., occlusion]) is used to make the recommendation.

Although omitted for conciseness, the preferred embodiments include every combination and permutation of the various system components and the various method processes, wherein the method processes can be performed in any suitable order, sequentially or concurrently.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

Additional or alternative embodiments implement the above methods and/or processing modules in non-transitory computer-readable media, storing computer-readable instructions. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device, with transitory computer-readable media, and/ or in any other suitable ways.

As a person skilled in the art will recognize from the previous detailed description and from the figures and claims, modifications and changes can be made to the preferred embodiments of the invention without departing from the scope of this invention defined in the following claims.

We claim:

1. A method for providing computer-aided decision guidance to a user, the method comprising, with a processing subsystem:
    receiving a set of data associated with a patient, the set of data comprising a set of images produced by an imaging modality located at a first point of care;
    processing the set of images with a set of trained machine learning models to check for a suspected pathology associated with the set of images;
    in response to detecting the suspected pathology, identifying a pathological region associated with the suspected pathology;
    identifying a second region separate and distinct from the pathological region;
    calculating a set of parameters associated with the second region;
    automatically and absent of human input during the method, selecting a single device from a set of multiple devices based on the set of parameters, thereby preventing delay of device selection associated with human input;
    automatically selecting the user and transmitting a notification comprising information associated with the selected single device to the user, wherein the user comprises a specialist associated with the suspected pathology;
    in response to receiving an input from the specialist, wherein the input comprises acceptance of the selected device, automatically triggering an action associated with transporting the selected device to the specialist, thereby minimizing a time until intervention for the patient with the selected device, wherein the action comprises an automated transmission of updates to a mobile device associated with the user, the updates related to transit of the selected device; and
    updating the set of trained machine learning models based on the intervention.

2. The method of claim 1, wherein processing the set of images further comprises processing the set of images with multiple sets of trained machine learning models, the multiple sets of trained machine learning models comprising the set of trained machine learning models, wherein each set of the multiple sets of trained machine learning models is associated with a potential pathology.

3. The method of claim 2, wherein the multiple sets of trained machine learning models are selected and retrieved for use based on a set of features associated with the set of data.

4. The method of claim 2, wherein each of the set of devices is associated with the suspected pathology.

5. The method of claim 1, further comprising receiving a second set of data associated with a healthcare facility, the healthcare facility associated with a second point of care remote from the first point of care.

6. The method of claim 5, wherein the second set of data received in response to assignment of treatment of the patient to the user.

7. The method of claim 6, wherein the second set of data comprises an inventory database.

8. The method of claim 7, further comprising automatically processing the inventory database to determine if the recommended device is present, wherein in an event that the recommended device is not present, the method further comprises at least one of: automatically contacting a medical device representative associated with the healthcare facility or determining a second recommended device associated with the treatment option.

9. The method of claim 1, wherein the set of parameters comprises a diameter measurement associated with the second region.

10. The method of claim 9, further comprising performing a segmentation process to reconstruct the pathological region and the second region, and determining the diameter measurement based on the segmentation process.

11. The method of claim 9, further comprising checking for the presence of a second diameter measurement having a value less than the diameter measurement, wherein in an event that the second diameter measurement is present, the selected device is further determined based on the second diameter measurement.

12. The method of claim 1, further comprising determining a second set of parameters associated with the pathological region, wherein the suspected condition is further determined based on the second set of parameters.

13. The method of claim 12, wherein the suspected pathology is a vessel occlusion comprising a clot, wherein the second set of parameters is associated with a set of features of a clot, the set of features comprising a clot perviousness.

14. A non-transitory computer readable medium storing instructions that, when executed by a computing system, cause the computing system to:
- receive a set of data associated with a patient, the set of data comprising a set of images produced by an imaging modality;
- process the set of images with a set of trained machine learning models to check for a suspected pathology associated with the set of images;
- in response to detecting the suspected pathology, identifies a region associated with the suspected pathology;
- calculates a set of parameters associated with the region;
- automatically and absent of human input, selects a single device from a set of multiple devices based on the set of parameters, thereby preventing delay of device selection associated with human input;
- automatically selects a user and transmits a notification comprising information associated with the selected single device to the user, wherein the user comprises a specialist associated with the suspected pathology;
- in response to receiving an input from the specialist, wherein the input comprises acceptance of the selected device, automatically triggers an action associated with facilitating receipt of the selected device by the specialist, thereby minimizing a time until intervention for the patient with the selected device, wherein the action comprises an automated transmission of updates to a mobile device associated with the user, the updates related to transit of the selected device; and
- updates the set of trained machine learning models based on the intervention.

15. The non-transitory computer readable medium of claim 14, wherein the region comprises a pathological sub-region and a second sub-region separate and distinct from the pathological sub-region.

16. The non-transitory computer readable medium of claim 15, wherein the set of parameters is calculated based on the second sub-region.

17. The non-transitory computer readable medium of claim 15, wherein the pathological sub-region is determined based on the suspected pathology, and the second sub-region is determined based on the pathological sub-region.

18. The non-transitory computer readable medium of claim 14, wherein the computing system further automatically establishes communication between a set of applications, wherein a first application of the set of applications is associated with the user, the user a specialist associated with treatment of the suspected pathology, and wherein a second application of the set of applications is associated with a second user, the second user a device sales representative associated with the selected device.

19. The non-transitory computer readable medium of claim 18, wherein the computing system further receives a second set of data associated with a healthcare facility, wherein the second set of data comprises an inventory database.

20. The non-transitory computer readable medium of claim 19, wherein the computing system further automatically processes the inventory database to determine if the recommended device is present, wherein in an event that the recommended device is not present, the computing system further automatically transmits a notification to the second application.

* * * * *